(12) United States Patent
Luo

(10) Patent No.: US 10,117,673 B2
(45) Date of Patent: Nov. 6, 2018

(54) METHODS AND DEVICES FOR SAFELY POSITIONING A NEEDLE SYRINGE IN A BODY CAVITY

(71) Applicant: FLATMED LLC, Cheyenne, WY (US)

(72) Inventor: Wen-Fu Luo, Taipei (TW)

( * ) Notice: Subject to any disclaimer, the term of this patent is extended or adjusted under 35 U.S.C. 154(b) by 293 days.

(21) Appl. No.: 14/947,997

(22) Filed: Nov. 20, 2015

(65) Prior Publication Data

US 2016/0144126 A1 May 26, 2016

Related U.S. Application Data

(60) Provisional application No. 62/091,199, filed on Dec. 12, 2014.

(30) Foreign Application Priority Data

Nov. 21, 2014 (TW) .............................. 103140451 A

(51) Int. Cl.
*A61B 17/34* (2006.01)

(52) U.S. Cl.
CPC .. *A61B 17/3401* (2013.01); *A61B 2017/3409* (2013.01)

(58) Field of Classification Search
CPC ........ A61M 5/3137; A61M 2005/3139; A61B 17/3401; A61B 2017/3409; A61B 17/3415; A61B 17/3409; A61B 2090/064; A61B 2205/583; A61B 17/3494

See application file for complete search history.

(56) References Cited

U.S. PATENT DOCUMENTS

| 4,062,354 | A | 12/1977 | Taylor et al. |
| 4,172,567 | A | 11/1979 | Patel |
| 4,215,699 | A | 8/1980 | Patel |
| 4,215,701 | A | 8/1980 | Raitto |
| 4,363,329 | A | 12/1982 | Raitto |
| 4,801,293 | A | 1/1989 | Jackson |
| 4,919,653 | A | 4/1990 | Martinez et al. |
| 5,024,662 | A | 6/1991 | Menes et al. |

(Continued)

*Primary Examiner* — Theodore Stigell
*Assistant Examiner* — Hamza Darb
(74) *Attorney, Agent, or Firm* — OPES IP Consulting Co. Ltd.

(57) ABSTRACT

The present disclosure provides a pressure-depending clutching device for locating and safely positioning a needle in a body cavity. The device is capable of automatically engaging and disengaging the needle from a driving force. The device has a body with an interior space, a pressure-sensing element and a force-receiving element. The pressure-sensing element, the force-receiving element, and the complementary force-sending element form a driving force engaging mechanism for coupling the force-applying structure to the needle during operation. Before the needle reaches the target body cavity, the pressure in the needle causes the clutching device to assume an "engaged" state. When the needle reaches the body cavity, the change in pressure causes the clutching device to assume a "disengaged" state, thereby, automatically positioning the needle in the cavity to avoid overshooting. Also provided are needle-and-syringe assemblies incorporating the disclosed clutching devices, methods for manufacturing the disclosed clutching devices.

9 Claims, 22 Drawing Sheets

(56) References Cited

U.S. PATENT DOCUMENTS

| | | |
|---|---|---|
| 5,207,647 A | 5/1993 | Phelps |
| 5,396,880 A | 3/1995 | Kagan et al. |
| 5,517,846 A | 5/1996 | Caggiani |
| 5,531,696 A | 7/1996 | Menes |
| 5,549,573 A | 8/1996 | Waskonig |
| 5,685,852 A | 11/1997 | Turkel et al. |
| 5,725,509 A | 3/1998 | Scarfone et al. |
| 5,836,914 A | 11/1998 | Houghton |
| 5,846,226 A | 12/1998 | Urmey |
| 5,902,273 A | 5/1999 | Yang et al. |
| 5,997,484 A | 12/1999 | Sugahara |
| 6,086,559 A | 7/2000 | Enk |
| 6,470,209 B2 | 10/2002 | Snoke |
| 6,565,542 B2 | 5/2003 | Kumar et al. |
| 6,773,417 B2 | 8/2004 | Fitzgibbons et al. |
| 6,925,323 B2 | 8/2005 | Snoke |
| 7,175,608 B2 | 2/2007 | Hasan et al. |
| 7,273,468 B2 | 9/2007 | Bedell |
| 7,549,996 B2 | 6/2009 | Vaisman et al. |
| 7,922,738 B2 | 4/2011 | Eichmann et al. |
| 8,043,229 B2 | 10/2011 | Mulvihill et al. |
| 8,328,738 B2 | 12/2011 | Frankhouser et al. |
| 8,137,312 B2 | 3/2012 | Sundar et al. |
| 8,197,443 B2 | 6/2012 | Sundar et al. |
| 8,608,665 B2 | 12/2013 | Vad et al. |
| 8,696,582 B2 | 4/2014 | Rohling |
| 8,777,871 B2 | 7/2014 | Frankhouser et al. |
| 8,777,944 B2 | 7/2014 | Frankhouser et al. |
| 8,814,807 B2 | 8/2014 | Hulvershorn et al. |
| 8,870,865 B2 | 10/2014 | Frankhouser et al. |
| 8,926,525 B2 | 1/2015 | Hulvershorn et al. |
| 8,992,439 B2 | 3/2015 | Mulvihill et al. |
| 2001/0047151 A1 | 11/2001 | Xian et al. |
| 2002/0198456 A1 | 12/2001 | Snoke |
| 2002/0007144 A1 | 1/2002 | Snoke |
| 2002/0198501 A1 | 12/2002 | Kumar et al. |
| 2003/0004460 A1 | 1/2003 | Bedell |
| 2003/0009135 A1 | 1/2003 | Fitzgibbons et al. |
| 2004/0186430 A1 | 9/2004 | Hasan et al. |
| 2007/0142766 A1 | 6/2007 | Sundar et al. |
| 2007/0213674 A1 | 9/2007 | Sundar et al. |
| 2007/0232993 A1 | 10/2007 | Sundar et al. |
| 2007/0244430 A1 | 10/2007 | Bedell |
| 2007/0244446 A1 | 10/2007 | Sundar et al. |
| 2008/0065028 A1 | 3/2008 | Vaisman et al. |
| 2008/0132926 A1 | 6/2008 | Eichmann et al. |
| 2009/0069712 A1 | 3/2009 | Mulvihill et al. |
| 2009/0099501 A1 | 4/2009 | Chang et al. |
| 2009/0131832 A1 | 5/2009 | Sacristan Rock et al. |
| 2010/0004558 A1 | 1/2010 | Frankhouser et al. |
| 2010/0191057 A1 | 7/2010 | Jansen et al. |
| 2010/0256483 A1 | 10/2010 | Wall et al. |
| 2011/0054353 A1 | 3/2011 | Hulvershorn et al. |
| 2011/0060229 A1 | 3/2011 | Hulvershorn et al. |
| 2011/0087173 A1 | 4/2011 | Sibbitt, Jr. et al. |
| 2011/0106052 A1 | 5/2011 | Chiang et al. |
| 2011/0218518 A1 | 9/2011 | Eichmann et al. |
| 2011/0224623 A1 | 9/2011 | Velez Rivera |
| 2011/0257660 A1 | 10/2011 | Jones et al. |
| 2011/0298628 A1 | 12/2011 | Vad et al. |
| 2012/0078164 A1 | 3/2012 | Mulvihill et al. |
| 2012/0209303 A1 | 8/2012 | Frankhouser et al. |
| 2012/0232564 A1 | 9/2012 | Daglow |
| 2012/0289820 A1 | 11/2012 | Rohling |
| 2013/0066200 A1 | 3/2013 | Frankhouser et al. |
| 2013/0072856 A1 | 3/2013 | Frankhouser et al. |
| 2013/0072857 A1 | 3/2013 | Frankhouser et al. |
| 2013/0085413 A1 | 4/2013 | Tsamir et al. |
| 2013/0204133 A1 | 8/2013 | Chiang et al. |
| 2013/0338577 A1* | 12/2013 | Al-Habaibeh .... A61M 25/0612 604/67 |
| 2014/0230824 A1 | 8/2014 | Lucchina et al. |
| 2014/0236085 A1 | 8/2014 | Landsberg |
| 2014/0276927 A1 | 9/2014 | Barker |
| 2014/0288408 A1 | 9/2014 | Deutsch |
| 2014/0288427 A1 | 9/2014 | Wall |
| 2014/0303494 A1 | 10/2014 | Janicki et al. |
| 2014/0323855 A1 | 10/2014 | Frankhouser et al. |
| 2014/0378904 A1 | 12/2014 | Senatore |
| 2014/0378905 A1 | 12/2014 | Senatore |
| 2015/0025363 A1 | 1/2015 | Hulvershorn et al. |

\* cited by examiner

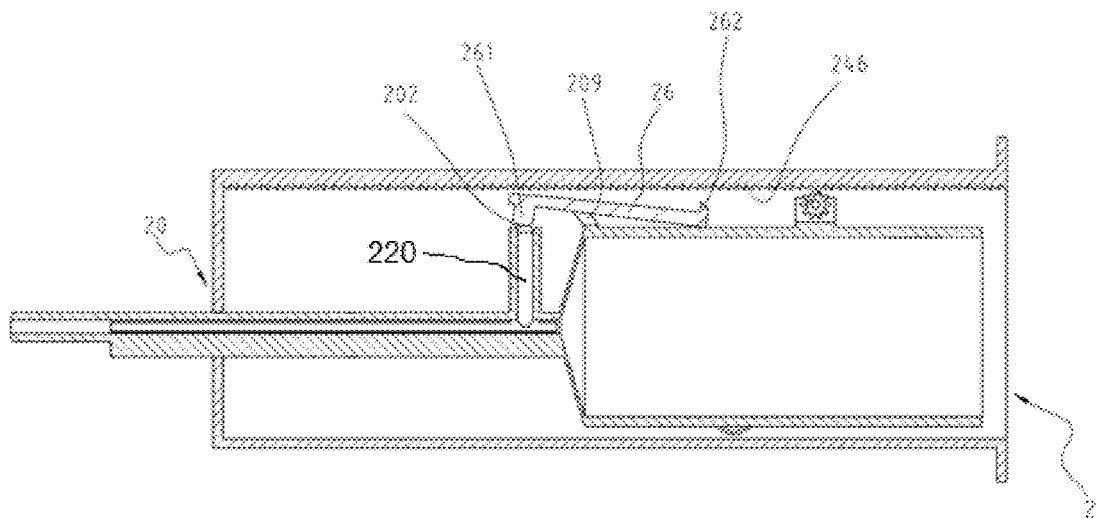
Figure 10-A
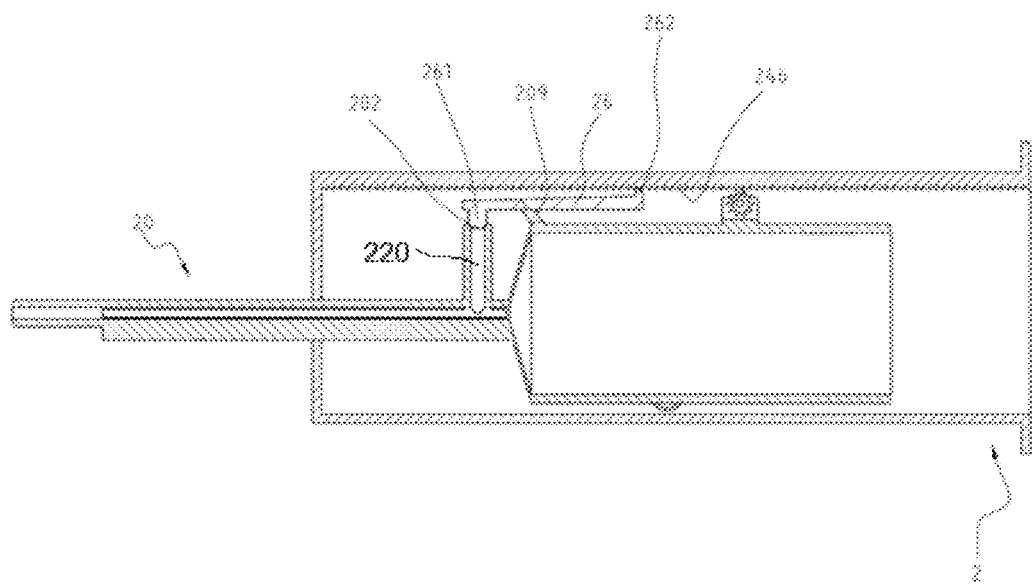
Figure 10-B

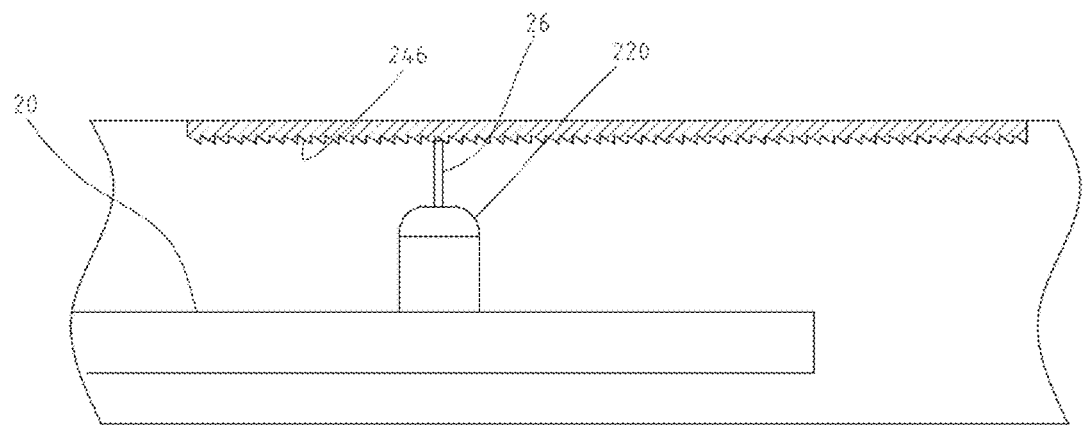
Figure 11-A
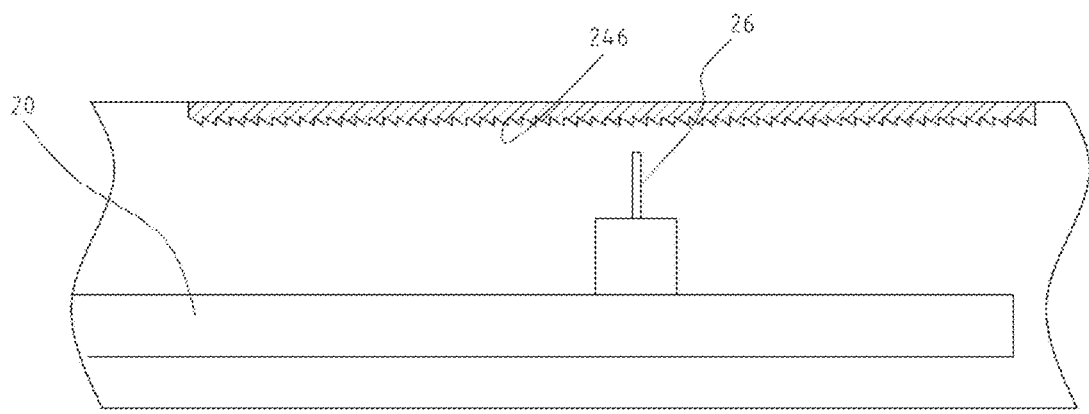
Figure 11-B

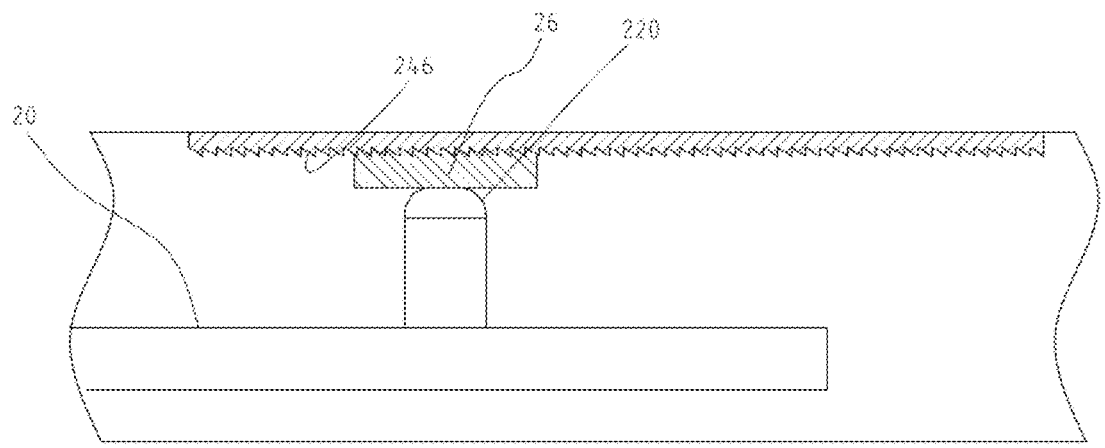
Figure 12-A
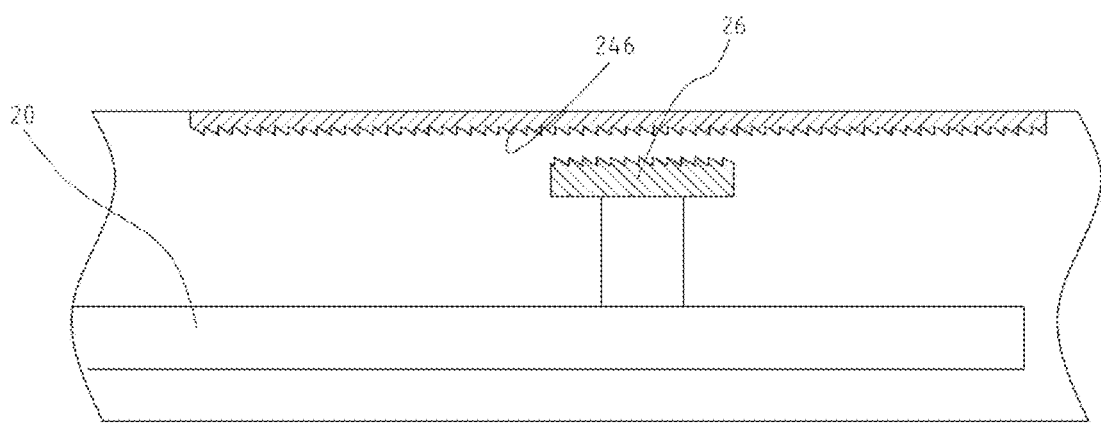
Figure 12-B

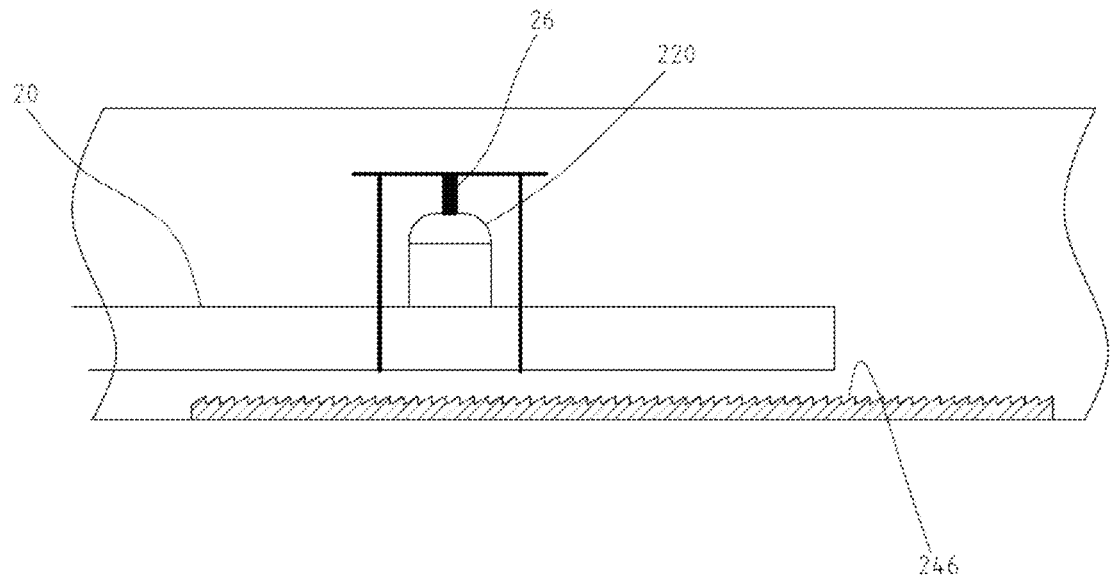
Figure 13-A
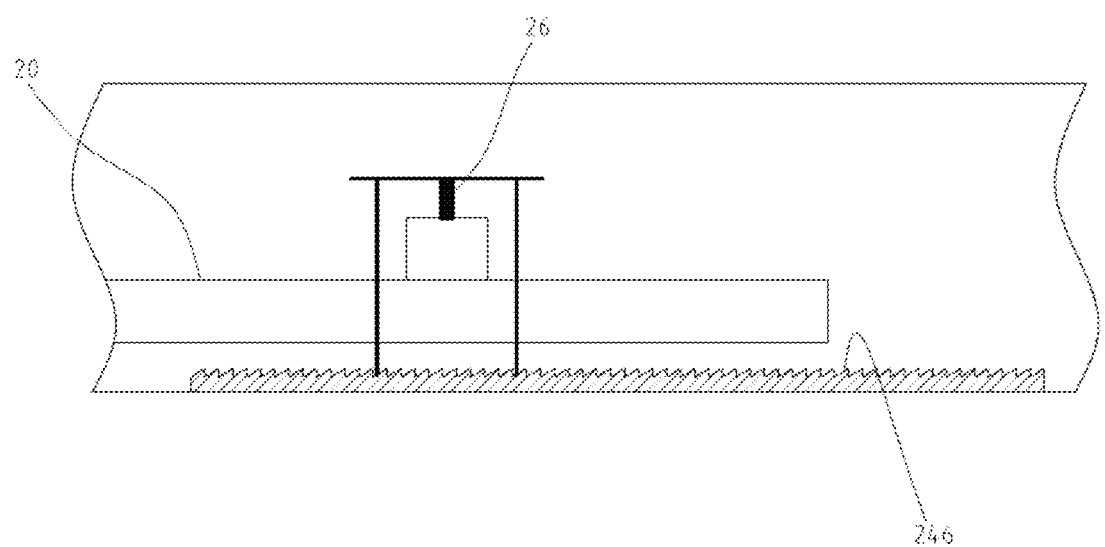
Figure 13-B

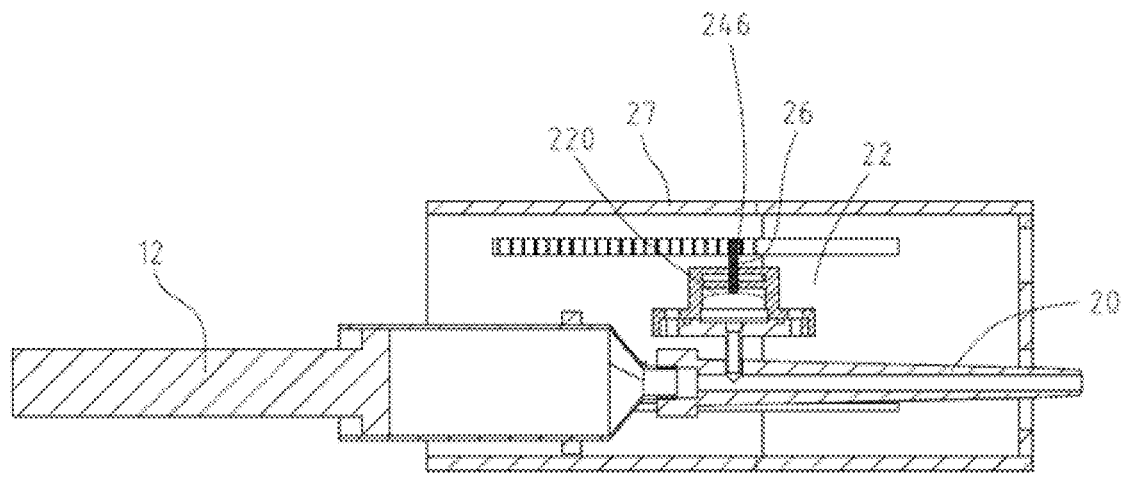
Figure 17-A
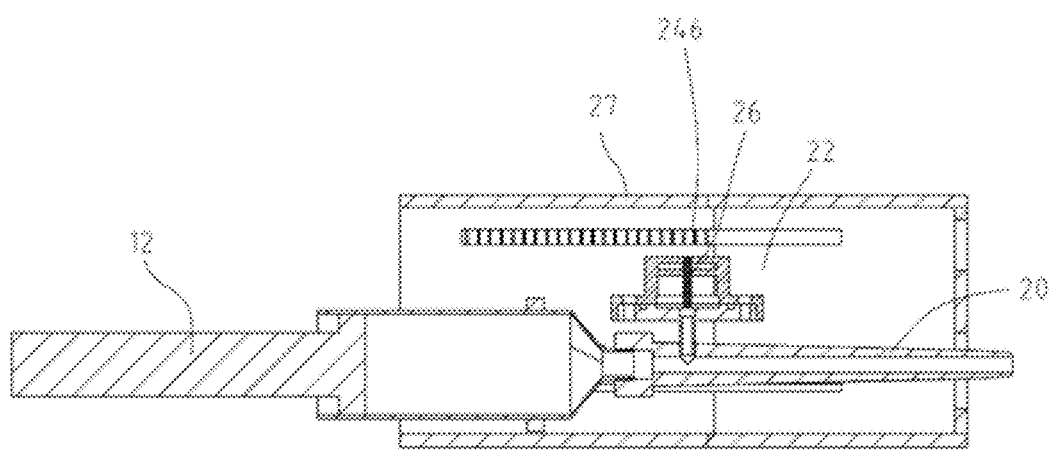
Figure 17-B

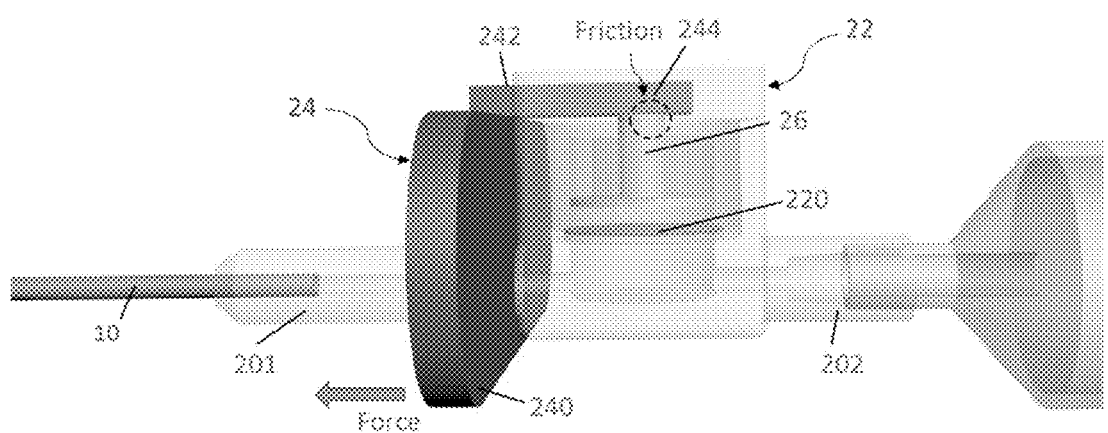
Figure 20-A

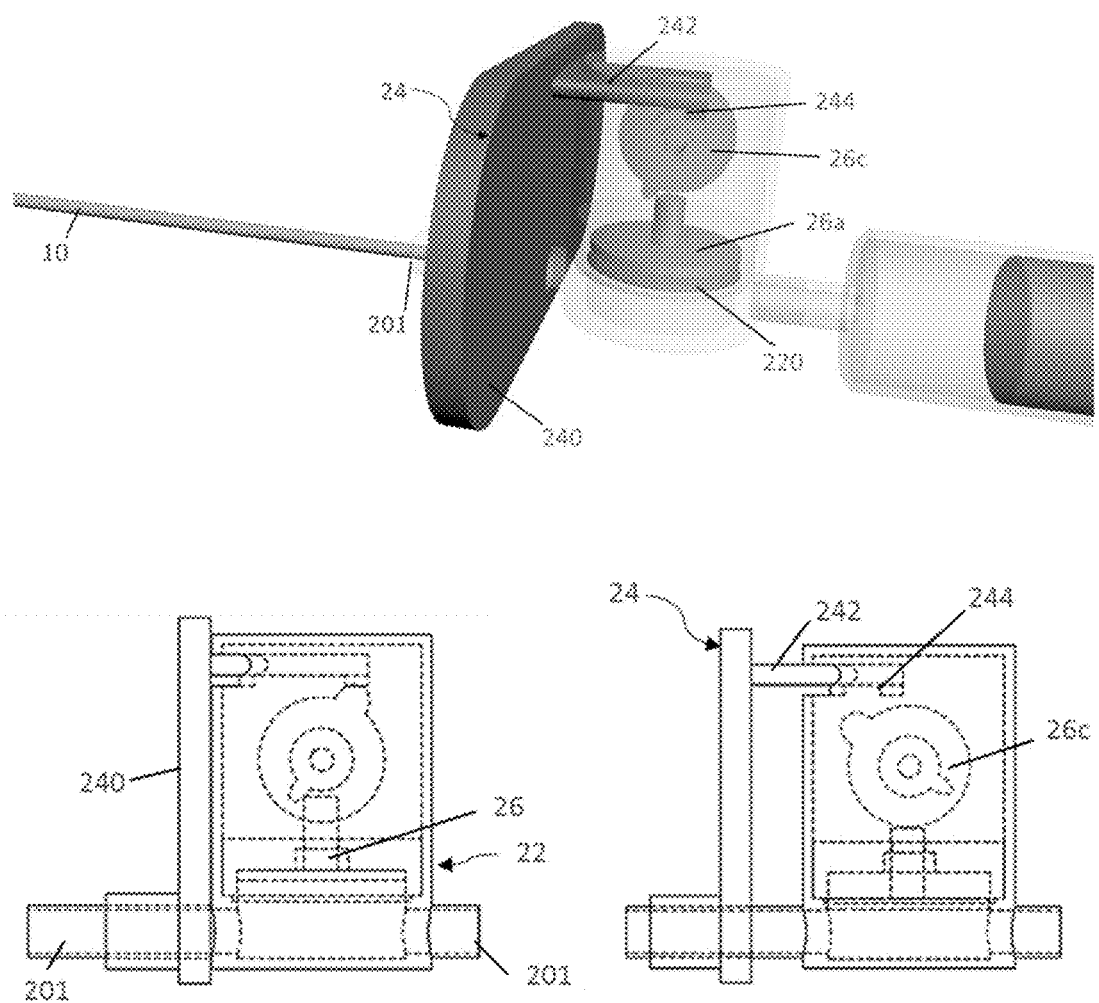
Figure 20-B

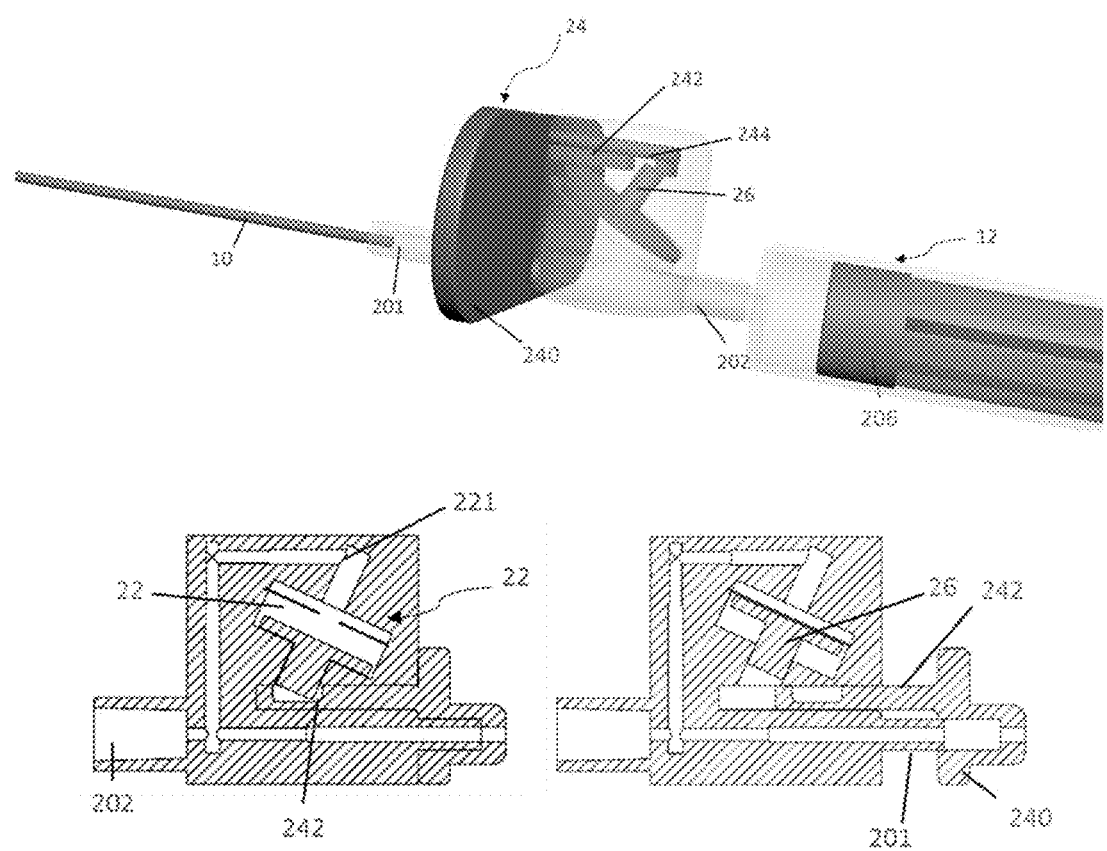
Figure 20-C

METHODS AND DEVICES FOR SAFELY POSITIONING A NEEDLE SYRINGE IN A BODY CAVITY

CROSS-REFERENCE TO RELATED APPLICATIONS

This application claims priority under 35 U.S.C. § 119(e) and the benefit of U.S. Provisional Application 62/091,199, filed Dec. 12, 2014, titled "POSITIONING DEVICE FOR NEEDLE SYRINGE". This application also claims foreign priority under 35 U.S.C. § 119(b) and the benefit of Taiwanese Patent Application number 103140451, filed Nov. 21, 2014, entitled, "A POSITIONING DEVICE FOR NEEDLE SYRINGE." The entire disclosures of the above referenced applications are each incorporated herein by reference.

FIELD OF THE INVENTION

This disclosure relates generally to the field of needle syringe positioning. More particularly, the present invention relates to devices and methods for safely positioning a needle syringe in a body cavity of a subject such as the epidural space.

BACKGROUND OF THE INVENTION

During medical procedures, locating and accessing a body cavity is often a required step for therapeutic, anesthetic, and diagnostic purposes. For example, procedures such as epidural injection, emergency tracheotomy, chest tube drainage, and percutaneous gastrostomy fistula all require accurately locating and accessing an implicated body cavity with a needle. These puncturing procedures bear high risk factors. When the needle is inserted too far or not far enough, catastrophic consequences can often result.

Using epidural injection as an illustrative example, this procedure requires positioning the tip of a needle precisely in the epidural space (also known as the epidural cavity) in order to administer pain-killing medicine. The epidural space is an anatomic space located at the outermost portion of the spinal canal, lying in between the ligamenta flava and the dura mater. In humans, the epidural cavity contains lymphatics, spinal nerve roots, loose connective tissue, fatty tissue, small arteries, and a network of internal vertebral venous plexuses. It is only about 3-5 mm wide. Inserting a needle beyond the epidural space can easily cause spinal cord injuries and other medical complications. Hence, it is very important to be able to accurately locate this body cavity.

Conventional methods for locating the epidural space generally rely on the manual skills of the operator (e.g. anesthesiologist, nurse, etc.). To perform an epidural injection using a conventional method, the operator will have to place the patient in a proper position first. Next, the operator will insert a needle into the spinal column of the patient. Once the tip of the needle enters the deeper part of the interspinous ligament, the operator will hold the needle in place and attach a saline or air filled syringe to the bub of the needle. Along with the syringe, a shaft or wing-shaped handle is typically mounted on the hub for the operator to apply an advancing force to drive the needle further into the body. As the operator pushes on the handle to move the needle forward, he will also push on the plunger of the syringe at the same time to maintain a pressure within the syringe barrel. Before the needle reaches the epidural space, there is no place for the air or saline to go, so a back pressure will be built up within the syringe barrel. This way, the operator will feel a sudden loss of resistance (LOR) when the needle reaches the epidural space as the air or saline is ejected into the epidural space. This sudden LOR allows the operator to know when to stop advancing the needle.

The above described conventional method is highly subjective, technically demanding, and prone to human error. It also takes much longer to locate the space as the operator must do it slowly to avoid missing the 3-5 mm space. Any slight inertial movement of the hand can easily move the needle pass beyond the epidural space, causing dural puncture and nerve damage.

Numerous attempts have been made in the art to address this problem. One approach focuses on providing a visual cue to assist the operator in knowing when the needle has reached the epidural space. For example, U.S. Pat. No. 7,175,608 B2 to Hasan teaches a representative device for locating the epidural space that utilizes a diaphragm to provide a visual cue to the operator for indicating when the needle has reached the epidural space. In Hasan's device, the diaphragm is adapted for pressurization such that when the device is pressurized, it bulges outwards to provide a visual indicator of the pressure change. Many other prior art methods and devices teach various means for similarly providing visual cues to indicate that the needle has reached the epidural space. However, these devices and methods do not solve the fundamental problem of operator error because they still must rely on the human operator to heed the warning and stop advancing the needle.

U.S. Pat. No. 8,715,234 B2 to Bethi teaches a device for locating a needle in a body cavity that purports to be able to automatically stop advancing the needle once the needle has reached the body cavity. The device works by balancing the frictional force between the needle and the ligament against the back pressure within the syringe barrel. It includes a syringe encased by a frame that is solely connected to the plunger of the syringe. While the needle is in the ligament, the back pressure within the barrel of the syringe will exceed the frictional force between the needle and the ligament so that when the operator pushes the plunger forward, the back pressure will act to advance the entire syringe/needle assembly forward. Upon entering the body cavity, the content of the syringe barrel will be released, thereby relieving the back pressure. At this point, the needle will be held in place by friction between the needle and the ligament while the plunger will advance to empty the contents of the syringe.

While the device of Bethi purports to be able to stop the needle upon entering the targeted cavity, it requires bulky construction and is not compatible with existing setup commonly found in medical facilities. In actual practice, Bethi's device further suffers from several other drawbacks. For example, because Bethi's device relies on balancing the air pressure in the syringe barrel against the friction between the needle and the ligament, the compressible nature of air will create an inherent instability in the needle-syringe assembly. This means that fine control of the needle is basically impossible, making it difficult for a user to precisely place the needle and further increasing the risk of damaging surrounding tissues. Moreover, the device relies on the negative pressure difference between the target cavity and the ligament; hence, it only works for cavities that have negative pressures relative to the ligament (e.g. the epidural space). For cavities that have higher pressure relative to the ligament (e.g. chest cavity), Bethi's device will not work.

Therefore, there still exists an urgent need for more universally applicable methods and devices of locating body cavities and placing needles therein without high risk of puncturing surrounding vital structures.

SUMMARY OF THE INVENTION

In the present invention, the problem of locating a body cavity and positioning a needle therein without accidentally overshooting the cavity to cause tissue damage is solved by a pressure-dependent clutching device capable of automatically engaging and disengaging the needle from a driving force based on the pressure differential inside and outside of the cavity.

In the context of the present invention, the term "clutching device" refers to a device capable of engaging and disengaging two working parts such that forces applied to one working part is transmitted to another working part only when the clutching device is placed in an "engaged" state. A "pressure-dependent clutching device" refers to a clutching device modulated by pressure. Such a device will be able to automatically switch between an "engaged state" and a "disengaged state" depending on whether a threshold external pressure has been encountered. Occurrence of such threshold pressure is herein referred to as the "threshold-crossing event." Using epidural injection as an illustrative example, when a needle-and-syringe assembly incorporating a pressure-dependent clutching device of the present invention is inserted into a patient, the pressure-dependent clutching device may assume an "engaged" state that couples the needle to a driving force to advance the needle further towards the epidural space. Upon reaching the epidural space, the needle will experience a pressure change, i.e. the threshold-crossing event. This pressure change will then trigger the pressure-dependent clutching device to automatically assume a "disengaged" state to uncouple the driving force from the needle. In this "disengaged" state, any driving force applied to the needle-and-syringe assembly will not be transmitted to the needle, thereby, ensuring that the needle does not move beyond the epidural space. With the aid of the clutching device, a user can simply apply a continuous driving force to the needle without worrying about overshooting the epidural space as the clutching device will act as safeguard to automatically disengage the driving force from the needle upon reaching the epidural space.

Accordingly, in one aspect, the present invention provides a pressure-dependent clutching device for automatically engaging and disengaging a needle from a driving force. Clutching devices in accordance with this aspect of the invention will generally include a body having an internal space, a pressure-sensing element defining a portion of a pressure chamber disposed in the interior space, and a force-receiving element operatively connected to the pressure-sensing element.

The term "operatively connected" as used herein encompasses both direct structural connection and indirect function connection so long as the connecting pair is configured to work together to accomplish a common function during operation. For example, a pin structurally connected to a disc that forms the shape of a piston may be considered to be operatively connected during a piston stroking operation. A pair of magnets configured to move in unison without physical contact may also be considered to be operatively connected in a force transmission operation that transmits a force from one magnet to the other.

During operation, the force-receiving element of the clutching device together with a complementary force-sending element forms a driving force engaging mechanism for engaging and disengaging the driving force. The force-sending element is operatively connected to a force-applying structure for receiving a driving force. When an operator applies a driving force to the force-applying structure, the driving force must go through a force transmission channel defined by the driving force engaging mechanism going from the force-sending element to the force-receiving element. This way, the driving force engaging mechanism can modulate the transmission of the driving force by engaging and disengaging the force-sending/receiving element pair. The driving force engaging mechanism is in turn modulated by the pressure-sensing element so that combined together, the pressure-sensing element and the driving force engaging mechanism work in conjunction to modulate the engaging and disengaging state of the clutching device according to an external pressure. The body of the device provides a housing for the various components of the device.

Numerous specific implementations of the clutching device are possible. In some embodiments, the clutching device may be implemented as a standalone unit apart from the needle and the syringe. In other embodiments, the clutching device may be implemented as an integral construct of the needle-syringe assembly. In some embodiments, the body of the clutching device may further include connection points for connecting to a needle and a syringe. For example, the body may include a first opening adapted to connect to a needle and a second opening adapted to connect to a syringe. The first opening may place the pressure-sensing element in pressure communication with the needle so that any change in the external pressure is immediately communicated to the pressure-sensing element.

The pressure-sensing element may be a mechanical structure, an electronic implement, an electromechanical implement, or a combination thereof. In some preferred embodiments, the pressure-sensing element is a mechanical structure. In one exemplary preferred embodiment, the pressure-sensing element is a flexible membrane able to switch between a concave and a convex shape. The flexible membrane may also form a wall of the pressure chamber. During operation, the chamber is placed in pressure communication with an external pressure via the needle so that when a threshold-cross event is encountered (i.e. a pressure change in the external pressure above or below a threshold), the membrane will switch shape from concave to convex and vice versa. Once the threshold-cross event is encountered, the change of state in the pressure-sensing element is relayed to the driving force engaging mechanism to cause a change in the engagement state of the clutching device so that the driving force applied to the force-applying structure may be allowed to engage or disengage the needle.

The force-applying structure is preferably external to the clutching device. In some preferred embodiments, the force-applying structure is a free-standing handle apart from the needle and syringe, more preferably a wing-shaped handle.

The driving force engaging mechanism may also be implemented with various structural configurations. In some embodiments, the force-receiving and force-sending element pair of the driving force engaging mechanism is a "pin-and-hole" pair structure. In such embodiments, the pin functions as the force-receiving element of the mechanism and is operatively connected to the pressure-sensing element. The hole functions as the force-sending element of the mechanism and is located on the force-applying handle such that when the external pressure calls for an "engaged" state, the pin is pushed into the hole to couple the needle with the force-applying handle. When the external pressure calls for a "disengaged" state, the pin is withdrawn from the hole to uncouple the handle from the needle.

The pin-and-hole pair is but only one illustrative pairing. Those skilled in the art will readily recognize that other complementary structural pairs may be advantageously used to implement the driving force engaging mechanism. Exemplary structural pairs may include, but not limited to, a hook and a hook catch in the form of a hole or a toothed rail track, a pair of complementary toothed tracks, and any other structures with complementary geometric shapes.

In some embodiments that use mechanical structural pairs to form the driving force engaging mechanism, a "sticky pin" problem may occur where the friction between the force-receiving element and the force-sending element may prevent withdrawal of the force-receiving element from the force-sending element. For example, when a pin-shaped force-receiving element becomes engaged with a hole-shaped force-sending element in a glove-over-fist fashion, the frictional force resulting from the surface contact between the surface of the pin and the inner wall of the hole may become too great for the pin to withdraw from the hole. Thus, in some preferred embodiments, the force-receiving element and the complementary force-sending element are configured such that the friction between the force-receiving element and the force-sending element is not sufficient to prevent withdrawal of the force-receiving element from the force-sending element. This may be accomplished by adopting geometries in which frictional force is minimized or eliminated between the force-receiving element and the force-sending element. For example, when the driving force engaging mechanism is a pin-and-hole pair, the pin may be configured to engage the hole at an angle so that the pin does not go into the hole completely, but instead wedges the hole at an angle. This way, the contact between the pin-and-hole pair does not create any friction to prevent withdrawal of the pin from the hole.

In another preferred exemplary embodiment, the force-sending element may include a gear mechanism having a first gear wheel and a second gear wheel bound together through a common shaft. In this embodiment, the first gear may be operatively connected to the force-applying structure while the second gear may be interfacing with the force-receiving element. In this embodiment, the amount of force needed to engage and disengage the force-receiving element from the gears may be adjusted through the ratio of the gear wheel sizes.

In the above described embodiments, the pressure-sensing element is described as being implemented with a mechanical structure. In embodiments where the pressure-sensing element is implemented with electronic, electromechanical, or other combinations, the general principle of coupling the external pressure change to a corresponding engagement state of the clutching device via the driving force engagement mechanism will remain the same. Those skilled in the art will be able to devise specific implementations following this general principle.

Construction material and shape of the various components of the clutching device are not particular limited. Exemplary material for forming the body may include plastics, metals, or any other suitable material commonly known in the art. The body may have regular geometric shapes such as cube or cylinder. It may also be configured to have irregular shapes to better accommodate the overall shape of the needle-and-syringe assembly.

Exemplary membrane material for forming the pressure-sensing element may include silicon rubber, polyvinyl chloride (PVC), thermoplastic rubber (TPR), polyethylene (PE), metal film, or any other suitable material known in the art.

While the above described clutching device is capable of automatically engaging and disengaging from a driving force without human input, in some use cases, it is still desirable to provide feedback to the human operator about the engagement state of the clutch or the pressure level sensed by the pressure-sensing element. Thus, in some further embodiments, the clutching device may further include a visual cue to indicate an "engaged" or "disengaged" state or a pressure state. Exemplary visual cue may include but not limited to a viewing window on the body of the device for a user to see the internal state of the clutch, or an electrical signal modulated by the state of the pressure sensing element. In one exemplary embodiment, a membrane pressure sensing element may be coated with an electrical conducting material such that the membrane effectively functions as an electrical switch. In such embodiments, when the membrane is caused to adopt one configuration, it may be brought into contact with a current, which in turn may be coupled with a signaling device such as an LED to indicate the state of the pressure. When the pressure causes the membrane to adopt an alternative configuration, the current is cut-off, resulting in the LED being turned off to indicate the change of state. It will be understood by those skilled in the art that this electrical signaling is not only suitable for providing a visual cue, but may also be configured to control the engagement and disengagement of the driving force engaging mechanism.

Preferably, clutching devices are implemented as independent units apart from the needle and syringe. Connection of the clutching device to the needle and syringe may be done directly via openings on the body of the device or indirectly via a connecting tube.

Connecting tubes suitable for connecting clutching devices of the present invention to a needle and a syringe will generally have a tubular body configured to have an end for connecting to a syringe and another end for connecting to a needle. In between the two ends, a portion of the connecting tube may be configured to connect to a clutching device of the present invention.

In still some other embodiments, the connecting tube may also be configured to include a frame for receiving a syringe.

Optionally, the clutching device may form an integral part of the syringe. In some exemplary embodiments, the body of the device may have an interior space configured to slidably receive a syringe. In such embodiments, the force-applying structure and the body of the clutching device form a single unit. The needle and syringe are coupled to the body of the clutching device via a driving force engaging mechanism formed by a pair of complimentary structures that includes the force-receiving element of the clutching device and the complementary force-sending element disposed on the body of the clutching device.

In another aspect, the present invention further provides a syringe-and-needle assembly capable of automatically disengaging from a driving force upon reaching a body cavity of a subject that has a pressure differential between the inside and the outside of the cavity. Embodiments in accordance with this aspect of the invention generally include a needle, a syringe, and a pressure-dependent clutching device as described above.

The types of needles and syringes are not particularly limited. Those skilled in the art will be able to choose the needle and syringe pair suitable for a particular purpose. In some preferred embodiments, the needle is preferably one suitable for epidural injection such as a Touchy needle or a Hustead needle, but not limited thereto. Exemplary syringes that may be used include loss-of-resistance (LOR) syringe, or a silicone syringe, but are not limited thereto.

During operation, it is desirable to prevent backflow of pressure towards the syringe barrel once the initial pressure is established within the pressure chamber of the clutching device so that loss of pressure can only occur due to pressure difference of the target cavity. Therefore, in some embodiments, clutching devices may further include a unidirectional valve to prevent backflow of air or fluid to the syringe end.

In yet another aspect, the present invention also provides a method for forming a pressure-sensitive clutching device suitable for automatically engaging and disengaging a needle from a driving force. Methods in accordance with this aspect of the invention will generally include the steps of forming a body having an interior space, placing a force engaging element and a pressure sensing element inside the body such that the force engaging element is operatively connected to the pressure sensing element and the pressure sensing element form a portion of a pressure chamber within the interior space. The pressure chamber is in pressure communication with an opening on the body of the device, wherein the opening is adapted for connecting to a needle. Embodiments for the force engaging element and the pressure sensing element are as described above.

In yet another aspect, the present invention also provides a method for positioning a needle in a body cavity of a subject defined by a structural layer of the subject. Embodiments in accordance with this aspect of the invention will generally include the steps of providing a needle-and-syringe assembly as described above; ensuring the pressure-dependent clutching devise is placed in an engaged state; and applying a continuous driving force on the force-applying structure to move the needle-and-syringe assembly forward until the pressure-dependent clutching device automatically disengages the driving force from the needle upon reaching the body cavity.

Other aspects and advantages of the invention will be apparent from the following description and the appended claims.

BRIEF DESCRIPTION OF THE DRAWINGS

FIG. 10-A shows a sectional view of the exemplary embodiment of FIG. 8. The driving force engaging mechanism is shown in a "disengaged" state.

FIG. 10-B shows another sectional view of the exemplary embodiment of FIG. 8. The driving engaging mechanism is shown in an "engaged" state.

FIG. 11-A shows a sectional view of a clutching device that illustrates an exemplary embodiment of a complimentary structural pair forming the driving force engaging mechanism. The mechanism is shown in an "engaged" state.

FIG. 11-B The same mechanism in FIG. 11-A is shown in a "disengaged" state.

FIG. 12-A shows a sectional view of a clutching device that illustrates another exemplary embodiment of a complimentary structural pair forming the driving force engaging mechanism. The mechanism is shown in an "engaged" state.

FIG. 12-B The same mechanism in FIG. 12-A is shown in a "disengaged" state.

FIG. 13-A shows a sectional view of a clutching device that illustrates yet another exemplary embodiment of a complimentary structural pair forming the driving force engaging mechanism. The mechanism is shown in an "engaged" state.

FIG. 13-B The same mechanism in FIG. 13-A is shown in a "disengaged" state.

FIG. 17-A shows a sectional view of an exemplary needle-and-syringe assembly incorporating a pressure-dependent clutching device in accordance with embodiments of the invention. The driving force engaging mechanism in this embodiment is shown in an "engaged" state.

FIG. 17-B The driving force engaging mechanism in the same embodiment in FIG. 17-A is shown in a "disengaged" state.

FIG. 19-A, FIG. 19-B, FIG. 19-C and FIG. 19-D each shows an exemplary step of the process in sequence.

FIG. 20-A: Illustrates an exemplary embodiment that experiences a "sticky pin" problem caused by friction.

FIG. 20-B illustrates one exemplary embodiment that overcomes the "sticky pin" problem shown in FIG. 20-A by utilizing a gear system.

FIG. 20-C illustrates another exemplary embodiment that overcomes the "sticky pin" problem shown in FIG. 20-A by utilizing an advantageous geometry.

DETAILED DESCRIPTION

Figure 1:
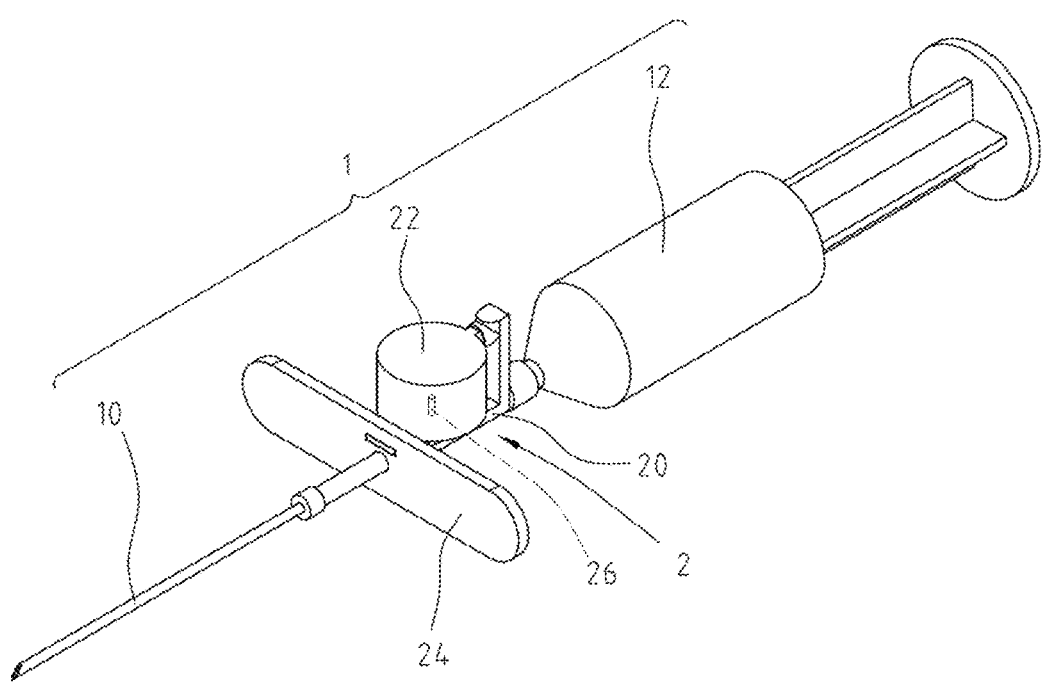
FIG. 1 shows an exemplary needle-and-syringe assembly incorporating a pressure-dependent clutching device in accordance with embodiments of the invention.

Referring first to FIG. 1, there is shown an exemplary embodiment of a pressure-dependent clutching device 2 connecting a needle 10 to a syringe 12 via a connecting tube 20. The clutching device 2 has a body with an interior space 22 and a pressure-sensing element disposed therein. The pressure-sensing element (not shown) is operatively connected to a force-receiving element 26 for engaging and disengaging a force-sending element that relays a driving force from a force-applying structure in the form of a wing-shape handle 24. Together, the needle 10, the wing-shaped handle 24, the clutching device 2, the connecting tube 20, and the syringe 12 form an exemplary needle-and-syringe assembly 1 capable of automatically disengaging a driving force depending on the external pressure encountered by the needle.

During operation, a user pushes on the handle 24 to apply a driving force to move the needle forward. Initially, the pressure within the internal space 22 of the clutching device 2 is sufficient to cause the force-receiving element 26 to engage the force-sending element so that the force applied to the wing-shaped handle 24 is transmitted to the needle 10 and moves the needle forward in concert the wing-shaped handle. When the needle 10 reaches the destination cavity, the pressure within the needle will be changed by the pressure difference inside of the cavity, which in turn will change the pressure within the pressure chamber 22 of the clutching device. The pressure chamber 22 is in pressure communication with the needle 10. If the destination cavity has a lower pressure than the pressure in the needle, this will result in a pressure drop within the pressure chamber 22. On the other hand, if the destination cavity has a higher pressure than the pressure in the needle, the pressure chamber 22 will experience a pressure jump. This concomitant pressure change will in turn cause the pressure-sensing element 220 to change state, resulting in the disengagement of the force-receiving element 26 from the force sending element, thereby, disengaging the driving force. At this point, moving force applied to the wing-shaped handle will no longer be transmitted to the needle, thereby achieving the desired outcome of positioning the needle in the targeted location.

Figure 2:
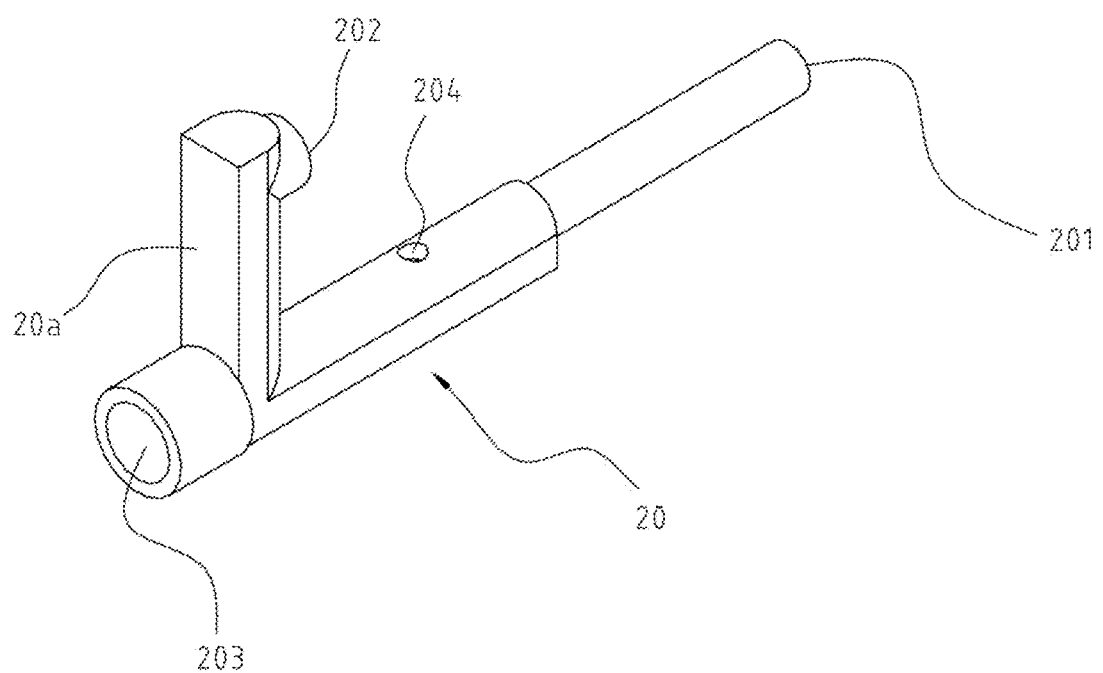
FIG. 2 shows an exemplary connecting tube in accordance with embodiments of the invention.
Figure 3:
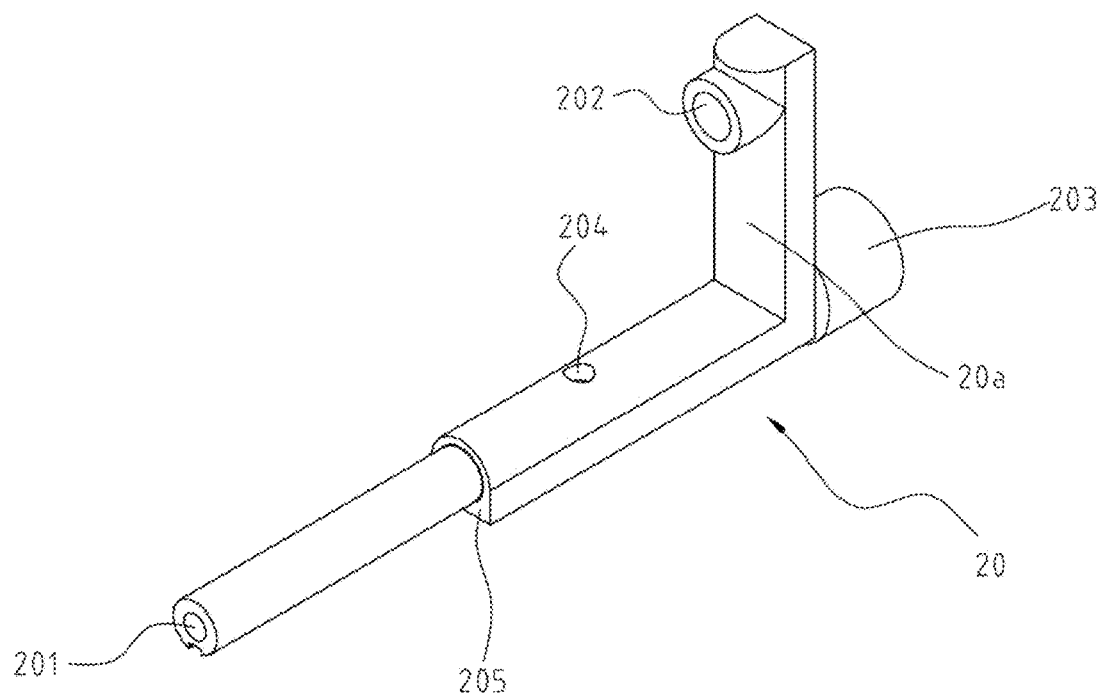
FIG. 3 shows another perspective view of the exemplary connecting tube of FIG. 2.

FIG. 2 shows a perspective view of the exemplary connecting tube 20 for connecting a needle to a clutching device and a syringe. In this exemplary embodiment, the connecting tube has a first opening 201 for connecting to a needle, a second opening 202 for connecting to a clutching device, and a third opening 203 for connecting to a syringe. In this exemplary embodiment, the connecting tube is configured to have an inverted T-shape, wherein the horizontal portion of the inverted "T" brings the needle and the syringe into fluid communication and the vertical portion 20a of the "T" brings the clutching device into pressure communication with the needle and the syringe. The horizontal portion of the "T" may also include a depression 204 that serves as the force-sending element for interfacing and engaging with the force-receiving element 26 of the clutching device. FIG. 3 shows another perspective view of the exemplary connecting tube 20.

Those skilled in the art will readily recognize that the size and shape of the openings 201 and 203 are to be adapted depending on the size and shape of the needle and syringe to be connected. In addition, it will also be recognized that the connecting tube is not limited to connecting only needles and syringes. It may also be used to connect, for example, an infusion pouch and an infusion tube. In such use cases, a clutching device may be used in conjunction with the connecting tube to indicate a change in pressure. It may also be coupled to a controller that regulates flow of infusion fluid.

Figure 4:
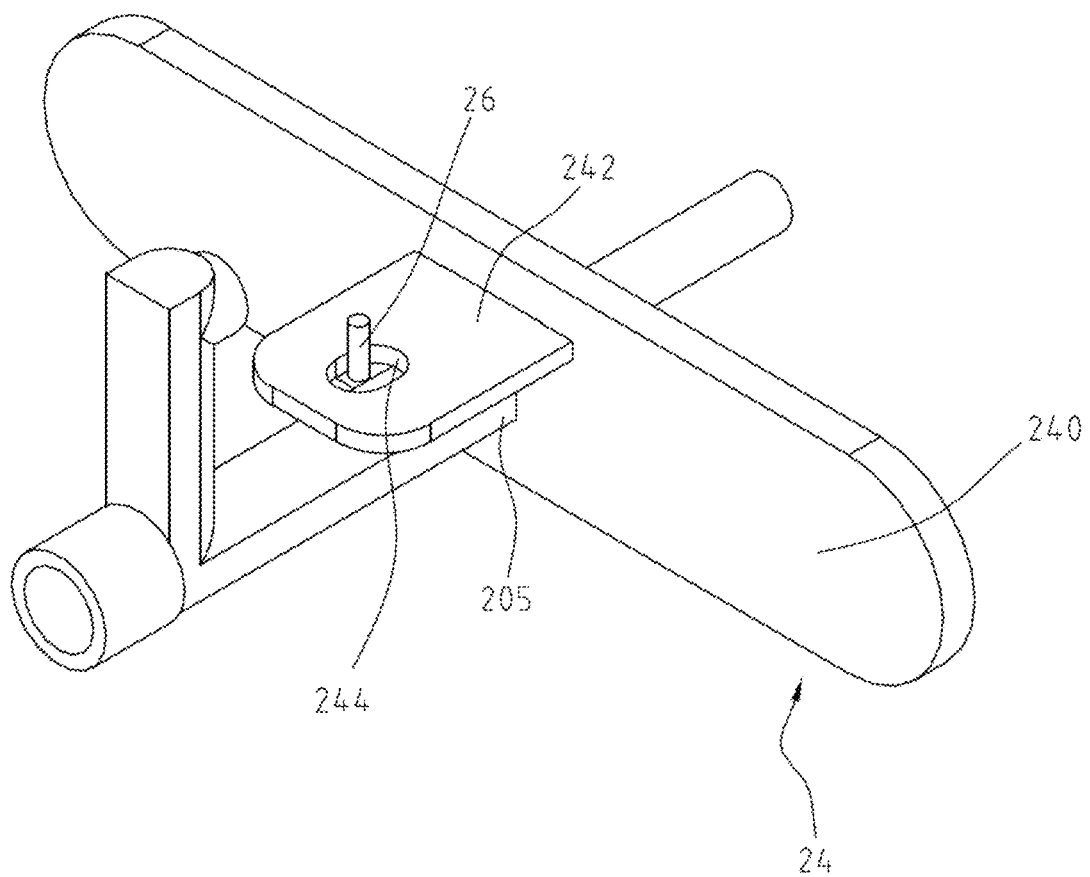
FIG. 4 shows a perspective view of an exemplary force-applying structure configured to be coupled with a clutching device in accordance with embodiments of the present invention.

FIG. 4 shows a perspective view of a wing-shaped handle 24 together with the exemplary connecting tube 20 of FIG. 1. The wing-shaped handle 24 has a wing 240 for applying a force and a locking panel 242 connected thereto. The locking panel further include a locking hole 244 functioning as the force-sending element for interacting with the force-receiving element 26 of the clutching device. In this particular embodiment, the force-receiving element is a locking pin that protrudes through the locking hole 242 into the depression 204 on the connecting tube. When the force-receiving element 26 (the locking pin) is in this position, the wing-shaped handle 24 is locked to the entire needle-syringe assembly so that a driving force applied to the wing-shaped handle is transmitted to the needle and moves the needle in concert with the wing-shaped handle.

Figure 5:
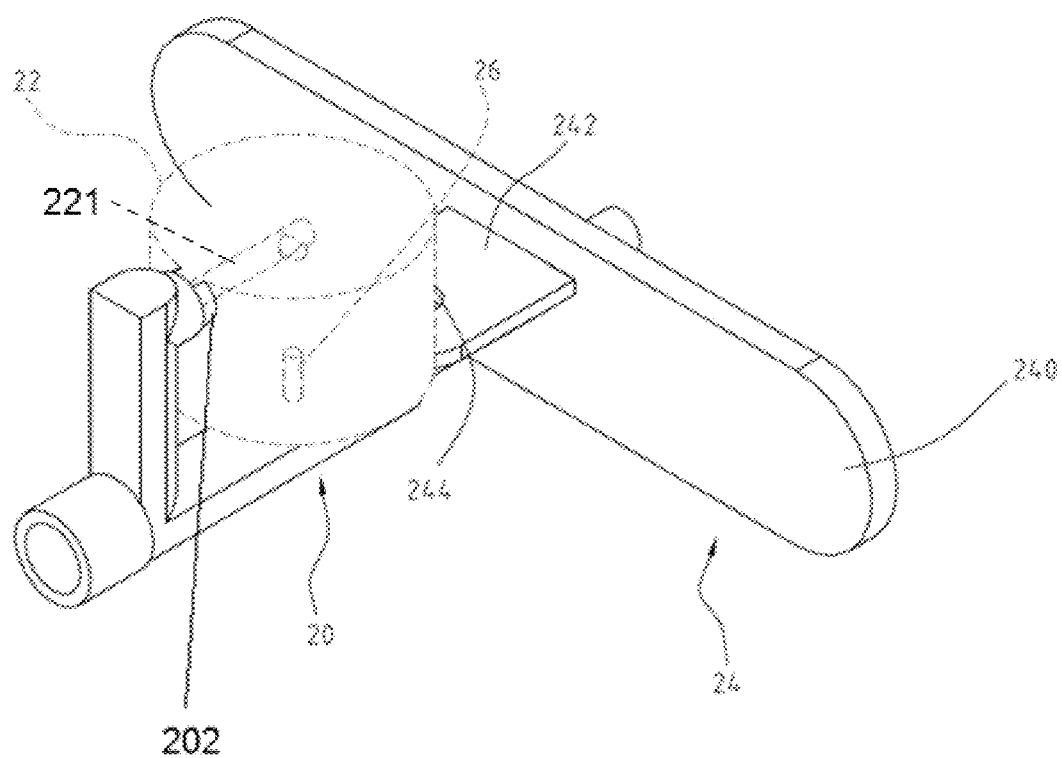
FIG. 5 shows a cutaway view of an exemplary clutching device illustrating the relationships between the various elements of the device in accordance with embodiments of the invention.

FIG. 5 shows the same perspective view of FIG. 4 with the addition of a see-through view of an exemplary positioning device. As shown in FIG. 5, the interior space of the body has a pressure chamber 22 that is connected to opening 202 of the connecting tube 20 via conduit 221 so that the pressure chamber 22 is placed in pressure communication with the needle. In this configuration, any pressure change within the needle will immediately be communicated to the pressure chamber 22 of the clutching device.

Figure 6:
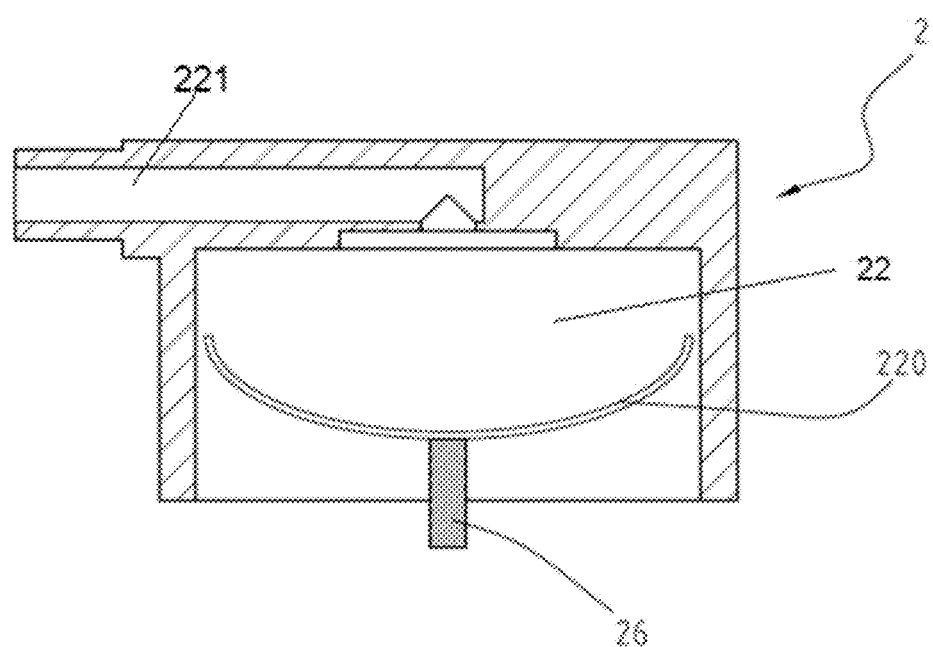
FIG. 6 shows a sectional view of an exemplary clutching device in accordance with embodiments of the invention with the force-receiving element in an "engaged" state.

FIG. 6 shows a sectional view of an exemplary clutching device 2 situated in a configuration as illustrated in FIG. 5. In this exemplary embodiment, a flexible film functions as the pressure-sensing element 220. Connected to the film 220 is a locking pin 26 acting as the force-receiving element. When pressure in conduit 221 is greater than pressure in the pressure chamber 22, the pressure-sensing element 220 assumes a concaved shape relative to the bottom of the clutching device. In this position, the locking pin 26 is pushed outwardly to form a protrusion on the bottom of the clutching device.

Figure 7:
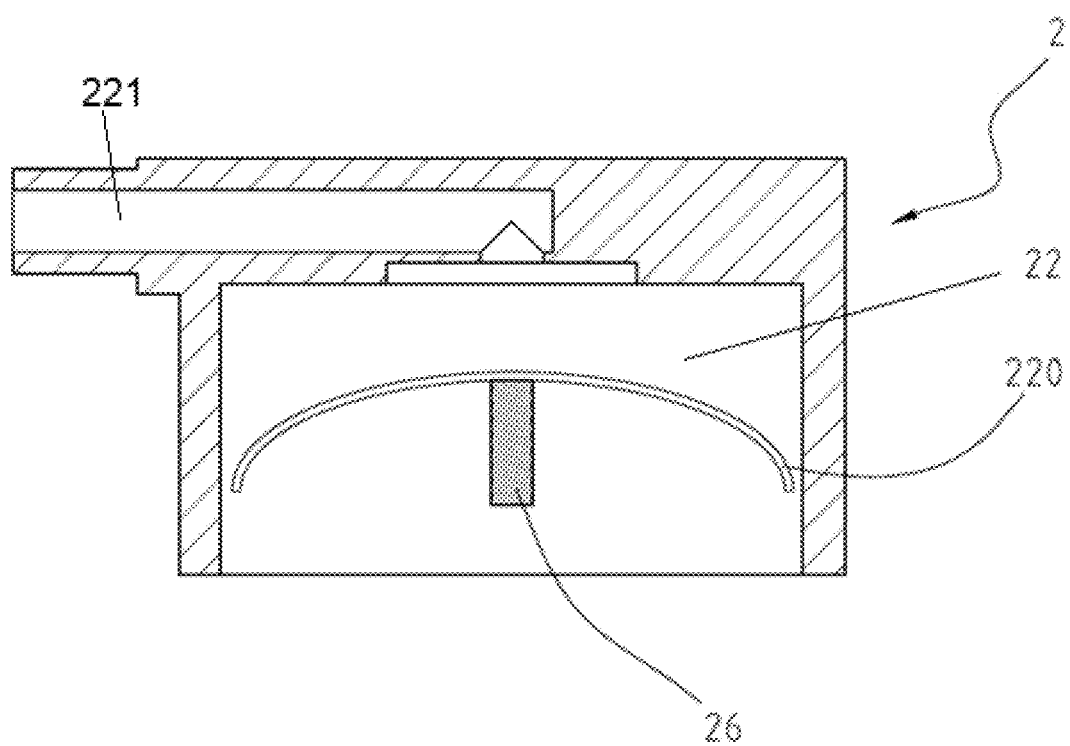
FIG. 7 shows another sectional view of an exemplary clutching device in accordance with embodiments of the invention with the force-receiving element in an "disengaged" state.

In contrast, as shown in FIG. 7, when the pressure in the conduit 221 is lower than the pressure in the pressure chamber, the pressure-sensing element 220 will assume a convexed shape relative to the bottom of the clutching device. The force-receiving element 26, being operatively connected to the pressure-sensing element 220, is pulled up and receeds into the interior of the clutching device 2.

Figure 8:
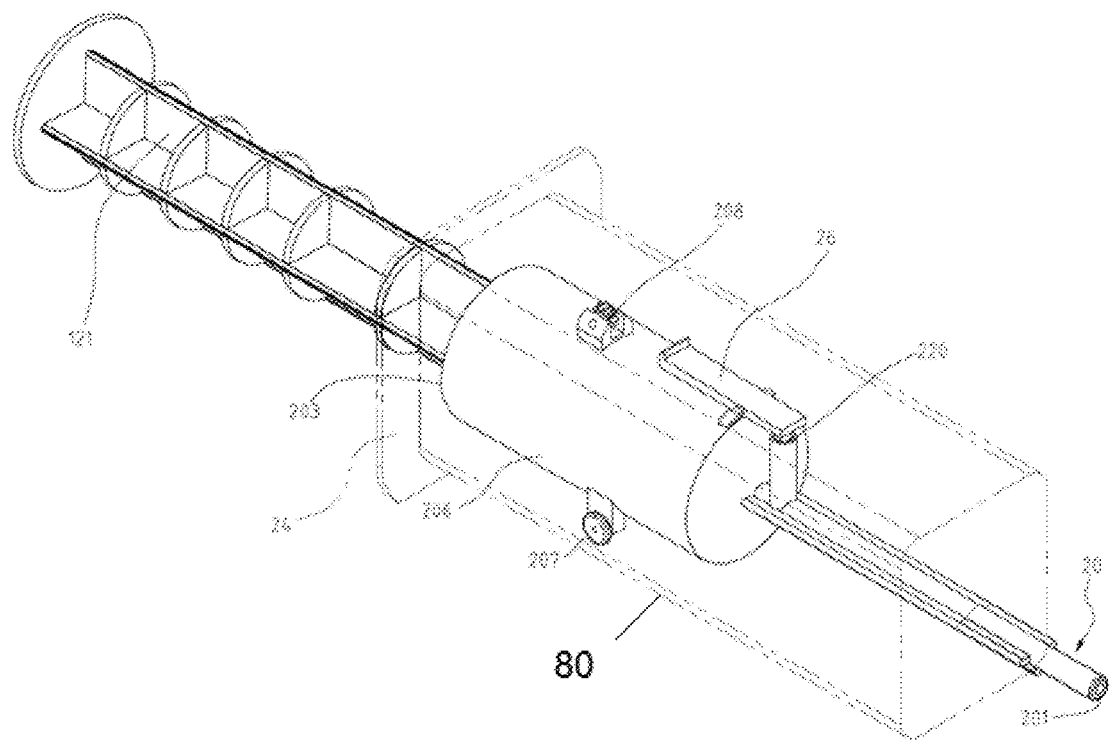
FIG. 8 shows a cutaway view of an exemplary pressure-dependent clutching device with integrated force-applying handle in accordance with embodiments of the invention.

FIG. 8 shows a perspective view of an exemplary alternative embodiment of a syrigne-and-needle assembly in accordance with the present invention. In this exemplary embodiment, the clutching device has a tubular encasing shell 80 that encloses a connecting tube 20 and a toothed rail track 246 (shown in FIG. 9). The connecting tube 20 has a first opening 201 adapted for connecting to a needle and a second opening 203 adapted for receiving a plunger 121. In this exemplary embodiment, the plunger-receiving end is configured to have a sufficiently large size to function as a syringe. Thus, the connecting tube 20 is configured to have a connecting portion and a syringe portion 206 leading to the second opening 203. For ease of discussion, the connecting tube 20 along with its syringe portion 206 and the plunger 121 may be referred to herein as the syringe-connecting tube assembly.

During operation, the syringe-connecting tube assembly is designed to be movable within the encasing shell 80. On the surface of the syringe portion 206, there are provided wheel 207 and toothed wheel 208 to facilitate motion of the syringe-connecting tube assembly within the interior space of the clutching device. The encasing shell 80 may further include a force-applying handle 24 to facilitate handling of the assembly.

Figure 9:
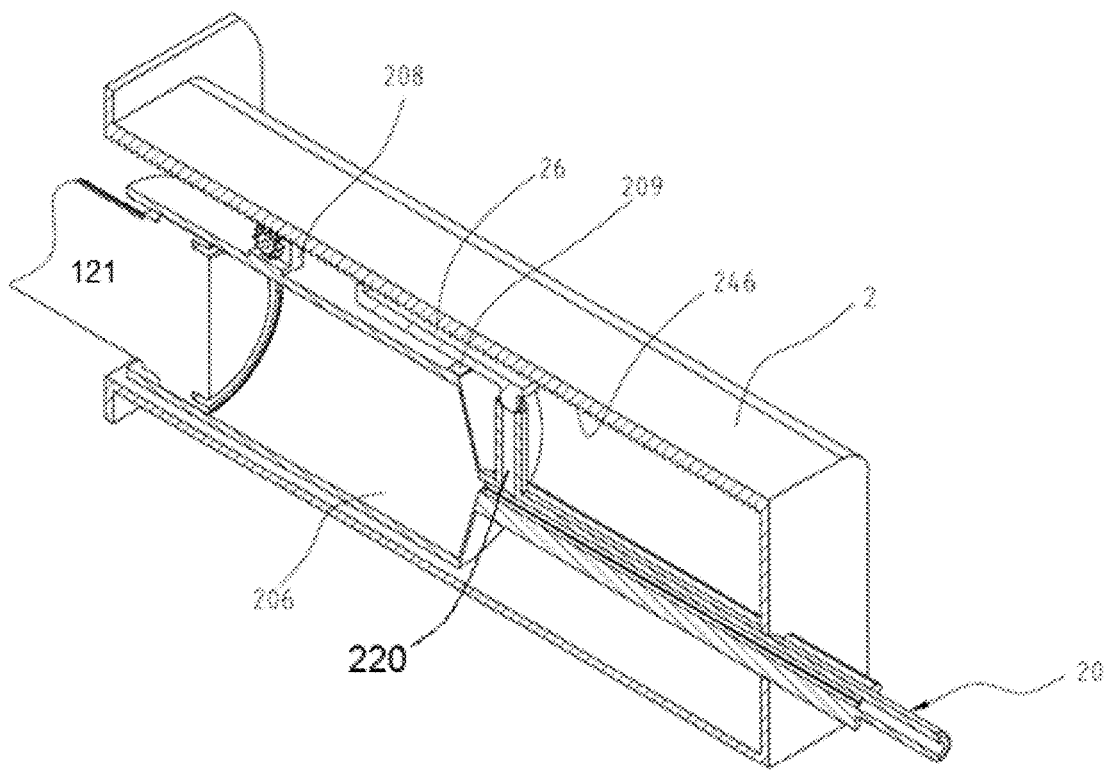
FIG. 9 shows a cutaway view of the exemplary embodiment of FIG. 8.

The exemplary embodiment of FIG. 8 is further illustrated in a cutaway view in FIG. 9. As illustrated in the figure, the interior wall of the positioning device 2 has a toothed rail track 246 for engaging the toothed wheal 208. A force-receiving element 26 is operatively connected to pressure-sensing element 220 and supported by a pivot bar 209.

During operation, connecting tube 20 is connected to the needle and transmits the pressure in the needle to sensing element 220 located at opening 202 (FIG. 20-A). The pressure-sensing element 220 in this exemplary embodiment is a movable pin and the force-receiving element 26 is a hooked bar pivoted on a pivot bar 209. The hooked bar has a first end 261 shaped like a hammer operatively connected to the sensing element 220 and a second end 262 shaped like a hook. When the pressure in the needle is above a threshold, the pressure sensing-element 26 (the movable pin) is pushed up against the first end 261 of the force interfacing element. This action causes the hook to be pivoted towards the surface of the syringe portion 206, thereby, disengaging from the toothed rail track 246 to allow the syringe-connecting tube assembly to move forward.

Referring to FIG. 10-B, when the pressure communicated to the pressure-sensing element drops below a threshold, the pressure-sensing element 220 will receed into the connecting tube, causing the first end 261 of the hooked bar to also drop toward the connecting tube. This action results in the hooked end 262 being pivoted towards the toothed rail track, thereby, engaging the toothed rail track to lock the syringe-needle assembly in place.

As illustrated above, the pressure-sensing element, the force-receiving element and the force-sending element together define a driving force engaging mechanism that functions to engage and disengage a driving force form the needle depending on the external pressure encountered by the needle. Those skilled in the art will readily recognize that numerous alternative implementation of the driving force engaging mechanism is possible. FIG. 11-A and FIG. 11-B illustrates an exemplary alternative embodiment having a locking pin 26 operatively connected to a pressure-sensing element 220. In this embodiment, the the locking pin 26 functions as the force-receiving element that engages and disengages the force-sending element, which in turn engages and disengages the syringe-needle assembly from the driving force. During operation of this embodiment, when the pressure in the connecting tube 20 is high, the pressure-sensing element will assume a convexing configuration (high pressure configuration) that pushes the locking pin 26 upward to engage the toothed rail track (FIG. 11-A). When the pressure in the connecting tube 20 is low, the pressure-sensing element will assume a flattened configuration (low pressure configuration) which in turn causes the locking pin to disengage from the toothed rail track, thereby, disengaging the needle-syringe assembly from the moving force (FIG. 11-B).

FIG. 12-A and FIG. 12-B illustrates another alternative embodiment that uses a toothed block as the force-receiving element 26 operatively connected to the pressure sensing element 220. The toothed block in this exemplary embodiment has a toothed portion complementary to the rail track 246. During operation of this embodiment, when the pressure in the connecting tube 20 is high, the pressure-sensing element 220 will assume a convexing configuration to push the toothed block 26 upward to engage the toothed rail track 246 (FIG. 12-A). When the pressure is low, the pressure-sensing element 220 will assume a flattened configuration so as to pull the toothed block 26 away from the toothed rail track 246, thereby, disengaging the syringe-needle assembly from the driving force.

FIG. 13-A and FIG. 13-B illustrates yet another alternative embodiment. In this exemplary embodiment, the force-receiving element 26 has a upside-down "U"-shaped cross-section. It may be a hollow cylinder, or simply two vertical bars connected by a horizontal bar. Any geometric shape having an upside-down "U"-shaped cross-section may suitable be used. During operation of this embodiment, a high pressure in the connecting tube 20 will cause the pressure-sensing element 220 to assume a convexing configuration sufficient to lift the upside-down "U"-shaped force-receiving element 26 so as to disengage the force-sending element from the toothed rail track 246 (FIG. 13-A). When the pressure is low, the pressure-sensing element 220 will assume a flattened configuration which in turn lowers the upside-down "U"-shaped force-receiving element 26 to engage with the toothed rail track 246. This action results in engagement of the driving force that moves the syringe-needle assembly.

Those skilled in the art will recognize that unlike previously describe embodiments, this embodiment engages the driving force when the pressure experienced in the needle/connecting tube is low and disengages the moving force when the pressure in the need/connecting tube reaches above a threshold level. Thus, this exemplary embodiment illustrates how one may adapt the clutching device to work with use cases involving both positive and negative pressure differences.

Figure 14:
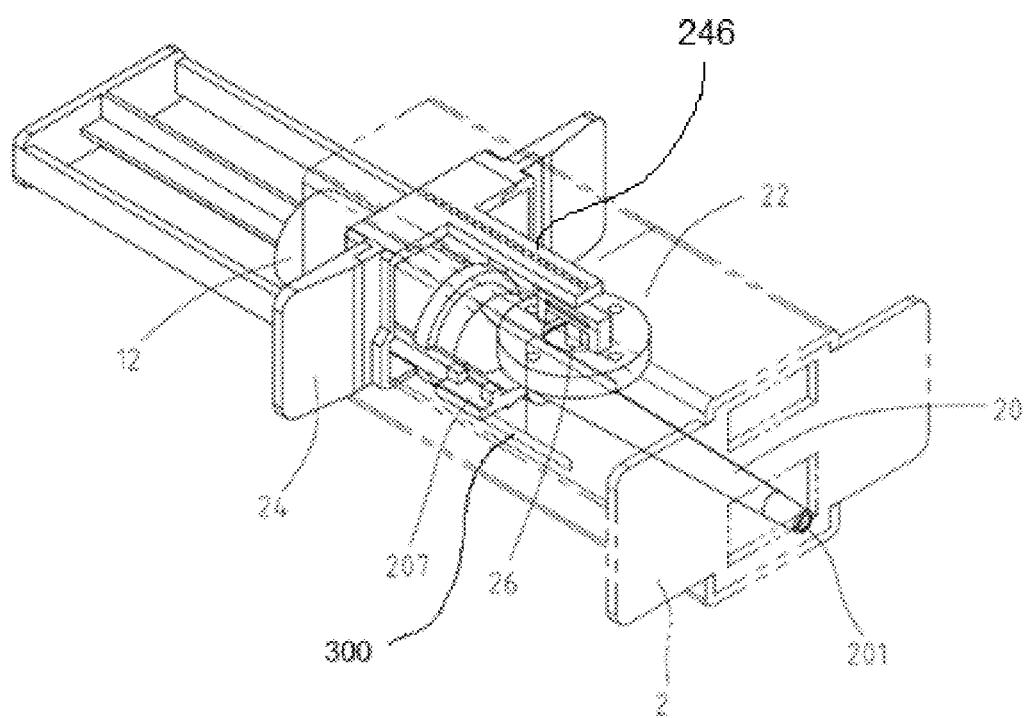
FIG. 14 shows a cutaway view of an exemplary needle-and-syringe assembly incorporating a locking device in accordance with embodiments of the invention.

FIG. 14 shows a cutaway view of another exemplary embodiment of a clutching device. In this exemplary embodiment, the body of the clutching device 2 has an interior space 22 configured to accommodate a syringe-connecting tube assembly 12 mounted on a slidable frame 210. The clutching device 2 further provides wing-shaped force-applying handles 24 for applying a moving force to the syringe-connecting tube assembly. Slotted sliding rails 300 are embedded in the body of the clutching device 2 for facilitating the sliding action of the syringe-connecting tube assembly within the interior space 22. In this exemplary embodiment, the sliding handle is configured as an independently movable frame with a slotted spine 246 for engaging the syringe-connecting tube assembly.

Figure 15:
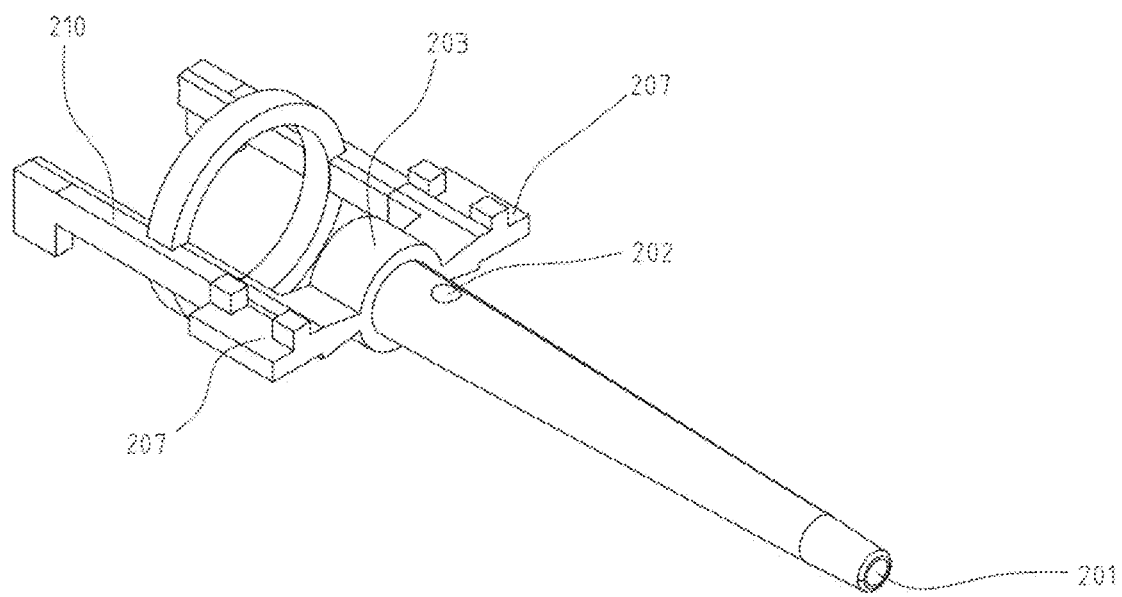
FIG. 15 shows a perspective view of an exemplary connecting tube with a syringe receiving frame in accordance with embodiments of the invention.

FIG. 15 shows a perspective view of the connecting tube 20 together with the syringe mounting frame 210. The connecting tube 20 has a first opening 201 for connecting to a needle, a second opening 202 for communicating pressure in the connecting tube to a pressure-sensing element 202, and a third opening 203 for connecting to a syringe. On the syringe mounting frame 210, there are sliding plates 207 for engaging slotted sliding rails 300 within the interior space 22 of the clutching device 2.

Figure 16:
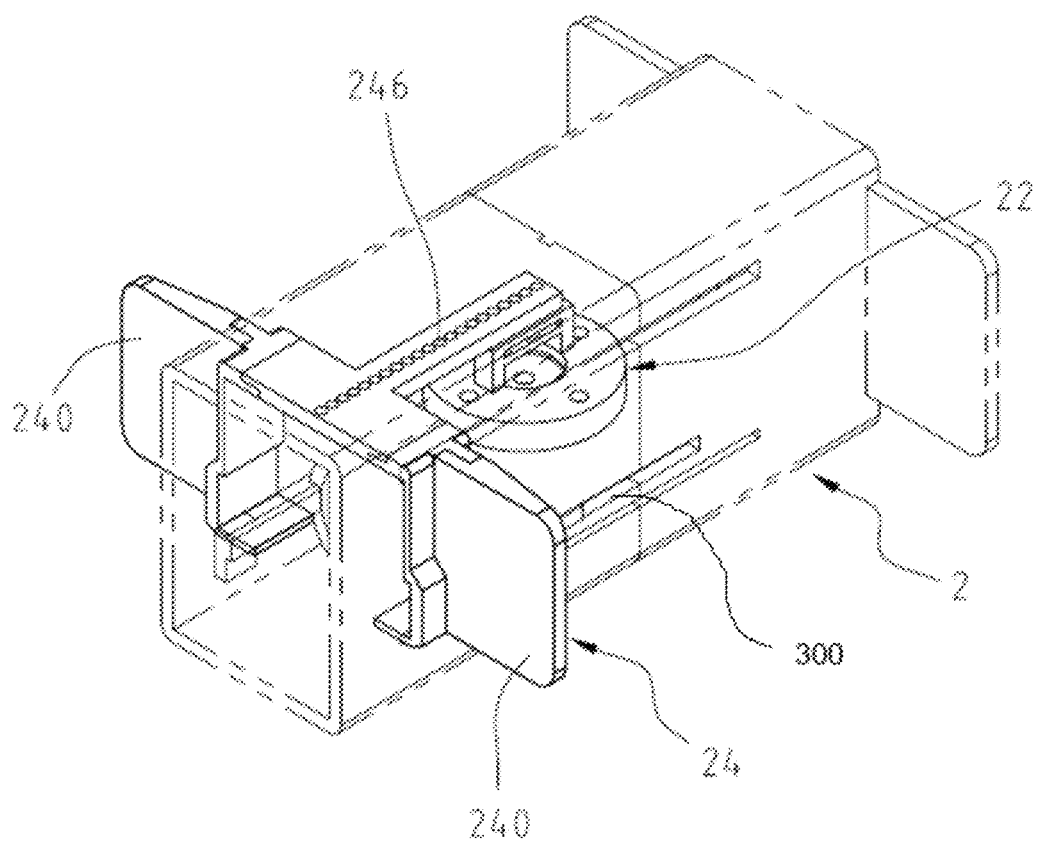
FIG. 16 shows a cutaway view illustrating the body of the clutching device and the force-applying structure in FIG. 14.

FIG. 16 shows a cutaway view of the positioning device 2 with the wing-shaped moving handle 24 mounted in the slotted sliding rails 300. When mounted, the moving handle 24 can be freely moved in the axial direction along the slotted rails by pushing on the wings 240 of the handle. A pressure-sensing element 220 with a force-receiving element operatively connected thereto is situated right below the slotted spine 246 of the moving handle 24. During operation of this embodiment, the pressure in the connecting tube 20 is communicated to the pressure-sensing element 220 via opening 202. A high pressure in the connecting tube 20 results in the pressure sensing element 220 adopting a convexing configuration (i.e. the high pressure configuration) that pushes the force-receiving element 26 (e.g. a locking pin) into a slot in the slotted spine 246 of the moving handle 24 (FIG. 17-A). In this configuration, the moving handle 24 and the syringe-connecting tube assembly are locked together so that the syringe-connecting tube assembly can be slided along the axial direction parallel to the slotted sliding rails 300 by pushing on the wings 240 of the moving handle 24. When the pressure in the connecting tube drops below a threshold level, the pressure-sensing element 220 is made to adopt a flattened configuration (i.e. the low pressure configuration) that withdraws the force-receiving element 26 (e.g. a locking pin) from the slotted spine 246. This configuration disengages the moving handle 24 from the syringe-connecting tube assembly so that any moving force applied to the moving handle will not be communicated to the syringe-connecting tube assembly (FIG. 17-B).

Figure 18:
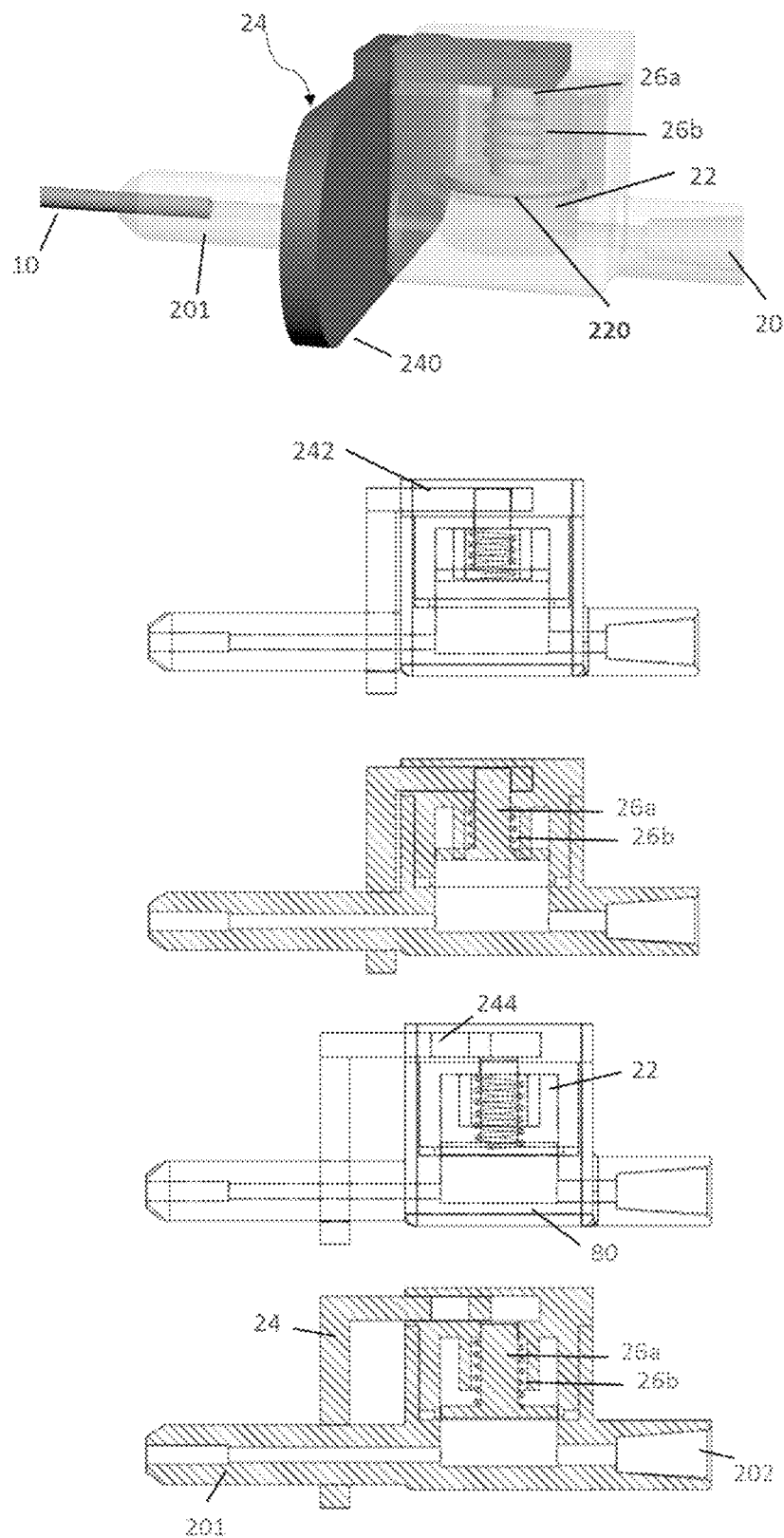
FIG. 18 shows a cutaway view of an exemplary pressure-dependent clutching device with the force-applying structure having a force sending element that is engaged by the force-sending element in accordance with embodiments of the invention.

FIG. 18 illustrates an exemplary preferred embodiment for a clutching device that requires only minimal modification to conventional epidural needles. In this embodiment, the clutching device is encased entirely in an enclosure 80. The enclosure 80 has a first opening 201 for connecting to a needle, a second opening 202 for connecting to a syringe, and a pressure chamber that connects the first opening 201 and the second opening 202. The pressure chamber is in pressure communication with a pressure sensing element 220, which may be a flexible film. The pressure-sensing element 220 is operatively connected to a force-receiving element 26. In a preferred embodiment, the force-receiving element is an inverted piston 26a with its rod pointing upwards. In some embodiments, the enclosure 80 has a throughhole from which the piston rod 26a may protrude to engage the locking panel 242 of the wing-shaped handle 24 via the locking hole 244. In other embodiments, the enclosure 80 may have a slot for the locking panel 242. In these embodiments, it is not necessary for the piston rod 26a to protrude through the enclosure 80.

To ensure the piston rod is initially in an "disengaged" position, a spring 26b may be fitted over the piston rod 26a. The spring 26b may be selected to set a threshold pressure at which the pressure-sensing element 220 is able to transition from a low pressure configuration to a high pressure configuration and vice versa.

Figure 19:
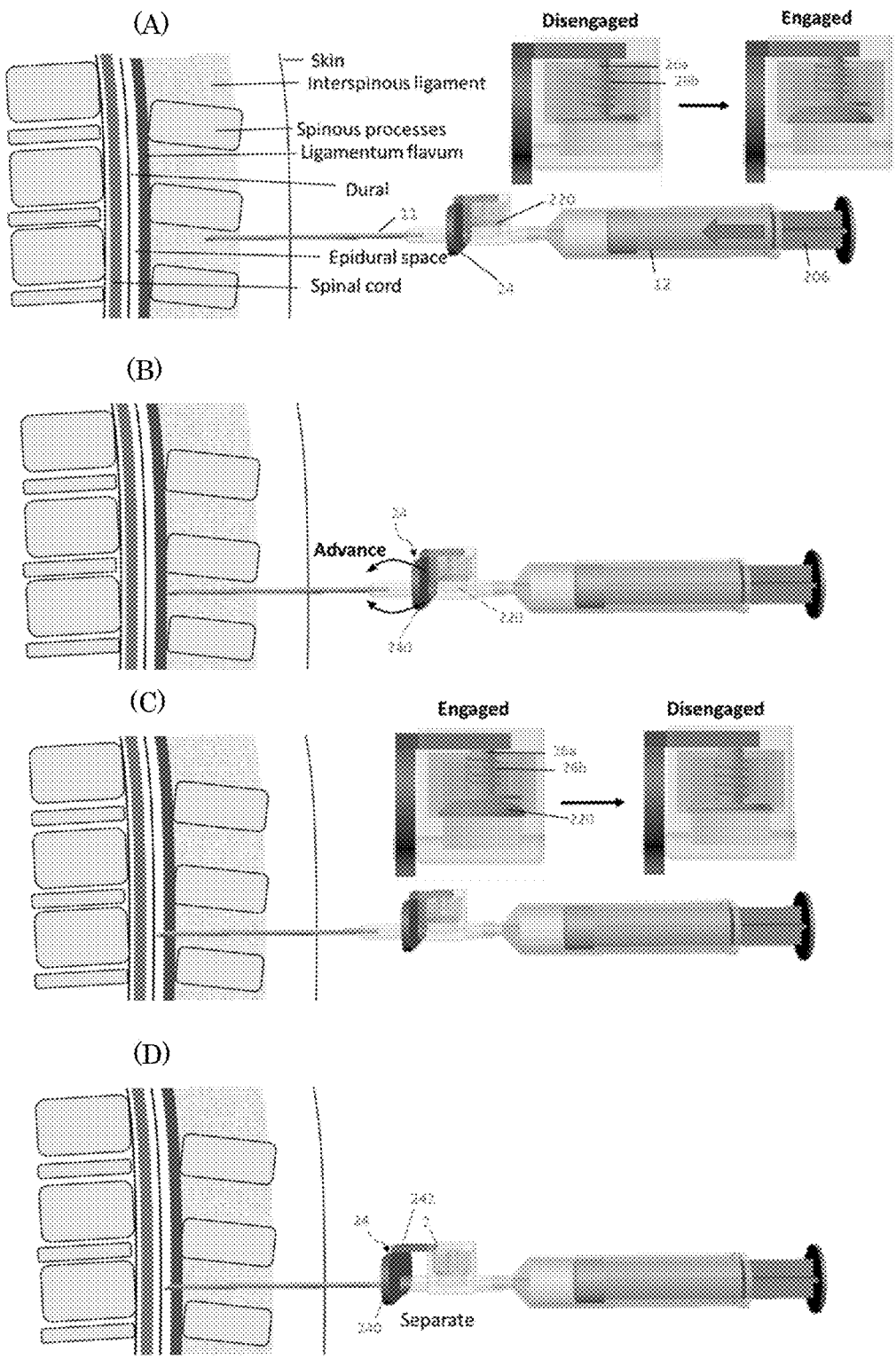
FIG. 19 illustrates the general process of locating and positioning a body cavity using an exemplary needle-and-syringe assembly endowed with a pressure-dependent clutching device in accordance with embodiments of the invention.

FIG. 19 shows an exemplary step-by-step process of positioning a needle in the epidural space using a needle-and-syringe assembly incorporating a clutching device as described above. In FIG. 19-A, a needle connected to a clutching device 2 outfitted with a wing-shaped handle 24 is first inserted into the ligament of a subject. At this stage, the pressure chamber is not yet pressurized so the piston rod 26a is in the "disengaged" position. Next, a syrigne is connected to the clutching device at opening 202. As the plunger is pushed forward into the syringe, the pressure chamber becomes pressurized to push the piston rod 26a into the "engaged" position. Once the piston rod 26a is in the "engaged" position, any driving force applied to the wing-shaped handle 24 will be transmitted to the needle so that the needle may be advanced into the ligament by pushing on the wing-shaped handle 24 as shown in FIG. 19-B.

Next, when the needle reaches the epidural space, the negative pressure within the epidural space causes the pressure chamber to depressurize. This change in pressure is immediately communicated to the pressure sensing element 220, which causes the piston rod 26a to revert to the "disengaged" position (FIG. 19-C). Once the piston rod 26a is returned to the "disengaged" position, the wing-shaped handle 24 and the needle-syringe assembly are no longer coupled together. At this point, any force applied to the wing-shaped handle will only move the handle forward, resulting in the separation of the handle 24 from the positioning device 2 (FIG. 19-D). The needle is securely lodged in place by friction, achieving the desired result of automatically positioning the needle in the epidural space and locking it in place.

In the above exemplary embodiments, one potential problem that may be encountered is that the piston rod 26a may not be disengaged easily due to the frictional force between the piston rod 26a and the locking panel 242 as illustrated in FIG. 20-A. This is referred to herein as the "stick pin" problem.

One possible way to overcome the "sticky pin" problem is to use a material with small frictional coefficient. Another possible way to overcome the "sticky pin" problem is to use a stronger spring. However, a strong spring may pose another challenger in that the pressure in the needle may not be large enough to overcome the spring, a condition necessary to raise the piston rod 242 in order to engage the wing-shaped panel 24.

FIGS. 20-B and 20-C each illustrates an alternative embodiment that may obviate the "sticky pin" problem. In FIG. 20-B, there is shown an exemplary embodiment that utilizes a gear system to overcome the "sticky pin" problem. In this exemplary embodiment, a large gear for engaging the handle and a small gear for engaging the pin are bound together via a common shaft. By choosing the appropriate gear ratios, the friction between the pin and the gear can be accounted for so that the frictional force does not create a sticky pin situation.

In FIG. 20-C, there is shown an exemplary embodiment that solves the "sticky pin" problem by positioning the inverted piston at an angle. During operation, as the user pushes the assembly forward, the piston is pushed upwards towards the chamber by the complementary pinhole. At the same time, the pressure in the chamber pushes the piston downwards towards the complementary pinhole. When the pressure in the chamber is high, the piston remains engaged with the complementary pinhole to hold the assembly in a "engaged" state. When the pressure in the chamer is relieved, the piston moves upwards to disengage from the complementary pinhole, thereby, placing the assembly into an "disengaged" state. By choosing an appropriate angle, the friction between the piston and the complementary pinhole can be taken into account so as to avoid a "sticky pin" situation.

All features of each of the aspects of the present invention apply to all other aspects mutatis mutandis. Variations, modifications, and other implementations of what is described herein will occur to those of ordinary skill in the art without departing from the spirit and the scope of the invention. Accordingly, the invention is to be defined not by the preceeding illustrative embodiments but instead by the spirit and scope of the following claims.

What is claimed is:

1. A pressure-dependent clutching device for automatically engaging and disengaging a force-applying structure so that a driving force will not drive a needle in an engaging state and will drive the needle in a disengaging state, wherein the driving force is from the needle depending on an external pressure encountered by the needle, comprising:

a body having an interior space;

a pressure-sensing element defining a portion of a pressure chamber disposed in the interior space for sensing the external pressure, said pressure-sensing element is adapted to switch between a first configuration corresponding to a first pressure state and a second configuration corresponding to a second pressure state; and a force-receiving element operatively connected to the pressure-sensing element, said force-receiving element is configured to have a complementary structure to a force-sending element that is operatively connected to the force-applying structure for a user to apply the driving force, wherein during operation, the needle is coupled to the force-applying structure via the pressure dependent clutching device and the pressure-sensing element is placed in pressure communication with the external pressure such that when the external pressure crosses a threshold level, the pressure-sensing element is caused to switch from one configuration to the other which in turn causes the force-receiving element to engage or disengage from the force-sending element resulting in the driving force applied at the force-applying structure drives or does not drive the needle.

2. The device of claim 1, wherein the pressure-sensing element comprises a membrane configured to adopt a concave or a convex shape corresponding to the external pressure.

3. The device of claim 1, wherein said force-receiving element comprises a pin and said force-sending element comprises a hole having a shape complementary to the pin such that the force-receiving element and the force-sending element form a pin-and-hole structural pair.

4. The device of claim 1, wherein said force-receiving element further comprises a spring.

5. The device of claim 1, wherein said force-applying structure is a handle.

6. The device of claim 5, wherein said force-applying structure is formed by a portion of the body.

7. The device of claim 1, wherein said force-receiving element comprises an inverted piston.

8. The device of claim 1, wherein said force-applying structure is a free-standing wing-shaped handle apart from the body of the device.

9. A syringe-and-needle assembly, comprising:
a syringe;
a needle operatively connected to the syringe;
a force-applying structure; and
the pressure-dependent clutching device of claim 1.

* * * * *

UNITED STATES PATENT AND TRADEMARK OFFICE
CERTIFICATE OF CORRECTION

PATENT NO. : 10,117,673 B2
APPLICATION NO. : 14/947997
DATED : November 6, 2018
INVENTOR(S) : Wen-Fu Luo It is certified that error appears in the above-identified patent and that said Letters Patent is hereby corrected as shown below:

In the Claims

Column 14, Lines 55-58, reads: A pressure-dependent clutching device for automatically engaging and disengaging a force-applying structure so that a driving force will not drive a needle in an engaging state and will drive the needle in a disengaging state...

Should read: A pressure-dependent clutching device for automatically engaging and disengaging a force-applying structure so that a driving force will not drive a needle in a disengaging state and will drive the needle in an engaging state...

Signed and Sealed this
Fifth Day of July, 2022

Katherine Kelly Vidal
*Director of the United States Patent and Trademark Office*